United States Patent [19]
Anderson

[11] Patent Number: 6,136,548
[45] Date of Patent: Oct. 24, 2000

[54] METHODS FOR IDENTIFYING USEFUL T-PA MUTANT DERIVATIVES FOR TREATMENT OF VASCULAR HEMORRHAGING

[75] Inventor: Stephen Anderson, Princeton, N.J.

[73] Assignee: Rutgers, The State University of New Jersey, New Brunswick, N.J.

[21] Appl. No.: 09/388,890

[22] Filed: Sep. 2, 1999

Related U.S. Application Data

[63] Continuation of application No. 08/686,959, Jul. 26, 1996, abandoned, and a continuation-in-part of application No. PCT/US95/15007, Nov. 22, 1995, which is a continuation-in-part of application No. 08/347,144, Nov. 22, 1994, Pat. No. 5,589,154.

[51] Int. Cl.$^7$ ............... G01N 33/53; G01N 33/00; C12N 15/09; C12N 9/64; A01N 37/18
[52] U.S. Cl. ............. 435/7.1; 435/69.2; 435/172.1; 435/226; 436/86; 514/2
[58] Field of Search ............... 424/9.2, 184.1; 435/7.1, 7.8, 69.1, 69.2, 172.1, 359, 212, 215, 226; 530/350, 380, 381, 382; 514/2; 436/86, 501

[56] References Cited

U.S. PATENT DOCUMENTS 5,366,886  11/1994  Anderson et al. ............... 435/226

OTHER PUBLICATIONS

Stewart, et al., "Characterization of the interactions of plasminogen and tissue and vampire bat plasminogen activators with fibrinogen, fibrin, and the complex of D–dimer noncovalently linked to fragment E", *J. Biol. Chem.*, 1998 273; 18292–18299.

Kingston, et al., In vitro stimulation of tissue–type plasminogen activator by Alzheimer amyloid β–peptide analogues, 1995 *Nature Medicine* 1(2); 138–142.

Merkle, et al., "Modulation of fibrin assembly and polymerization by the β–amyloid of Alzheimer's disease" 1996 *Blood Coagulation and Fibronolysis* 7(6); 650–658.

*Primary Examiner*—Jose' G. Dees
*Assistant Examiner*—Michael G. Hartley
*Attorney, Agent, or Firm*—Law Offices of Jane Massey Licata

[57] ABSTRACT

Methods for preventing or treating vascular hemorrhaging such as that incident to thrombolytic therapy, or characteristic of Alzheimer's and related diseases are provided. Such methods provide improved thrombolytic therapy to individuals who receive such therapy, and permit the diagnosis and treatment of diseases, such as Alzheimer's Disease, that are characterized by the deposition of amyloid deposits.

1 Claim, 3 Drawing Sheets

METHODS FOR IDENTIFYING USEFUL T-PA
MUTANT DERIVATIVES FOR TREATMENT
OF VASCULAR HEMORRHAGING

CROSS-REFERENCE TO RELATED APPLICATIONS

This application is a continuation of U.S. patent application Ser. No. 08/686,959, filed Jul. 26, 1996, now abandoned, which is a continuation-in-part of PCT/US95/15007, filed Nov. 22, 1995, which is a continuation-in-part of U.S. application Ser. No. 08/347,144, filed Nov. 22, 1994, now U.S. Pat. No. 5,589,154, all of which are herein incorporated by reference.

FIELD OF THE INVENTION

The invention relates to an improved method for preventing or treating vascular hemorrhaging. More specifically, the invention concerns methods for providing improved thrombolytic therapy to individuals who receive such therapy, and for diagnosing and treating diseases, such as Alzheimer's Disease, that are characterized by the deposition of amyloid deposits. The invention further relates to therapeutic agents for the prevention of the vascular and cellular damage induced by amyloid deposits. This invention was funded with Government funds (R01AG10462 and R01AG11525). The Government has certain rights in this invention.

BACKGROUND OF THE INVENTION

I. PLASMINOGEN AND PLASMINOGEN ACTIVATORS

The serum protein, plasminogen, plays an integral role in the proteolytic dissolution (or fibrinolysis) of blood clots. Plasminogen is an inactive "proenzyme." It has a specific affinity for fibrin, and thus becomes incorporated into blood clots as they form. Plasminogen's proteolytic activity is released by "plasminogen activators" ("PA") that specifically cleave the molecule to yield the active protease, plasmin. Plasmin is capable of digesting the fibrin threads of blood dots, as well as other substances involved in creating blood dots, such as fibrinogen, factor V, factor VIII, prothrombin, and factor XII (for review, see Danø, K. et al., *Adv. Canc. Res.* 44:139–266 (1985), herein incorporated by reference)).

Plasmin is a serine protease, and exhibits substantial amino acid and mechanistic homology with trypsin, chymotrypsin, and pancreatic elastase. Plasmin has a relatively broad trypsin-like specificity, hydrolyzing proteins and peptides at lysyl and arginyl bonds (Castellino, R. W. et al., *Meth. Enzymol.* 80:365–380 (1981); Danø, K. et al., *Adv. Canc. Res.* 44:139–266 (1985)).

Two classes of natural mammalian plasminogen activators have been described: urokinase-type plasminogen activator and tissue-type plasminogen activator ("t-PA") (Danø, K. et al., *Adv. Canc. Res.* 44:139–266 (1985); Devlin, et al., PCT appl. WO88/05081; Kasaia et al., U.S. Pat. No. 5,098,840; Hayashi, S. et al., U.S. Pat. No. 4,851,345; Sasaki et al., U.S. Pat. No. 4,258,030; Hayashi, S. et al., U.S. Pat. No. 5,004,609; Pyke, C. et al., *Amer. J. Pathol.* 138:1059–1067 (1991); Madison, E. L. et al., *Nature* 339:721–724 (1989); Blasi, F. et al.,*J. Cell. Biol.* 104:801–804 (1987)). These two classes of molecules can be distinguished immunologically, by tissue localization, and by the stimulation of their activity by fibrin. In addition, a third plasminogen activator, streptokinase, has also been described. Streptokinase differs from urokinase and t-PA in that it is a bacterial protein produced by the *streptococci*.

Urokinase-type plasminogen activator (UK) is a multi-domain protein with one domain being a trypsin-like serine protease (Castellino, R. W. et al., *Meth. Enzymol.* 80:365–380 (1981); Danø, K. et al., *Adv. Canc. Res.* 44:139–266 (1985); Straβburger, W. et al., *FEBS Lett.* 157:219–223 (1983)). This protease domain converts plasminogen to plasmin by cleavage at an arginyl residue (Castellino, R. W. et al., Meth. Enzymol. 80:365–380 (1981); Danø, K. et al.,*Adv. Canc. Res.* 44:139–266 (1985)). The amino acid sequence and three-dimensional structure of several serine proteases, including trypsin, chymotrypsin, and elastase have been deduced (Danø, K. et al.,*Adv. Canc. Res.* 44:139–266 (1985); Straβburger, W. et al., *FEBS Lett.* 157:219–223 (1983)).

Urokinase is synthesized in the kidneys, and can be recovered from urine. It is initially produced as a single chain protein, "pro-urokinase" that can be proteolytically cleaved by plasmin into an active two-chain protein (Devlin, et al., PCT appl. WO88/05081).

Tissue-type plasminogen activator (t-PA) is produced by the cells that line the lumen of blood vessels or endothelial cells. Like urokinase, t-PA is also initially produced as a single-chain molecule (Rijken, D. G. et al., *J. Biol. Chem.* 256:7035–7041 (1981); Pennica, D. et al., *Nature* 301:214–221 (1983)).

The known plasminogen activators differ significantly in characteristics such as their biological half-lives and their preference for fibrin. All three classes of activators have been widely used as thrombolytic agents for the treatment of thrombosis in myocardial infarction, stroke, arterial occlusion, etc. (Kasai et al., U.S. Pat. No. 5,098,840; Hayashi et al., U.S. Pat. No. 5,004,609; Hayashi et al., U.S. Pat. No. 4,851,345; Sasaki et al., U.S. Pat. No. 4,258,030).

The administration of t-PA for the treatment of thrombosis in myocardial infarction, stroke, arterial occlusion, and other cardiovascular diseases reflects the production of minute blood clots which are formed during the disease process. The presence of such clots significantly increases the criticality of the disease, and increases its morbidity. Since t-PA is able to activate plasminogen to plasmin, it is capable of initiating the cascade of events needed to dissolve undesired blood clots. As such, its administration significantly decreases the mortality associated with myocardial infarction and other acute cardiovascular conditions.

Unfortunately, the use of t-PA and streptokinase has been associated with the occurrence of hemorrhages in some individuals (Pendlebury, W. W. et al., *Annls. Neurol.* 28:210–213 (1989); Wijdicks, E. F. M. et al., *Stroke* 24:554–557 (1993); Kase, C. S. et al., *Annls. Intern. Med.* 112:17–21 (1990); Molinari, G. F. *Stroke* 24:523–526 (1993);), particularly when administered with anti-clotting factors such as coumarin or heparin. This phenomenon has limited the use of t-PA and streptokinase to treat cardiovascular disease in certain classes of patients, notably, the elderly (Topol, E. J. et al., *New Engl. J. Med.* 327:45–47 (1992); De Jaegere, P. P. et al., *J. Amer. Col. Cardiol.* 19:289–294 (1992); Gore, J. M. et al., *Circulation* 183:448–459 (1991)).

II. ALZHEIMER'S DISEASE AND RELATED CONDITIONS

Alzheimer's Disease ("AD") is a progressive disease of the human central nervous system. It is manifested by dementia in the elderly, by disorientation, loss of memory, difficulty with language, calculation, or visual-spatial skills, and by psychiatric manifestations. It is associated with degenerating neurons in several regions of the brain. Alzheimer's Disease is reviewed by Price, D. L. et al. (*Clin. Neuropharm.* 14:S9–S14 (1991)); Pollwein, P. et al. (*Nucl. Acids Res.* 20:63–68 (1992)); Regland, B. et al. (*Med. Hypoth.* 38:11–19 (1992)) and Johnson, S. A. (In: Review of Biological Research in Aging, Vol. 4., Rothstein, M. (Ed.), Wiley-Liss, NY, 163–170 (1990)).

Pathologically, Alzheimer's Disease is recognized by the presence of intracellular tangles, and an extracellular 39–43 amino acid peptide known as the β/A4-amyloid peptide (Price, D. L. et al., *Clin. Neuropharm.* 14:S9–S14 (1991); Podlisny, M. B. et al., *Science* 238:669–671 (1987); Currie, J. R. et al., *J. Neurosci. Res.* 30:687–689 (1991)). The fibrils formed by this peptide are concentrated in amyloid deposits in the extracellular space of the brain parenchyma and in the vascular elements of the brain and the pia-arachnoid (Currie, J. R. et al., *J. Neurosci. Res.* 30:687–689 (1991)). All cases of Alzheimer's Disease show such deposition of amyloid in brain parenchyma.

The amyloid peptide is produced from the proteolytic cleavage of an amyloid precursor protein ("APP") which is encoded by the APP gene located on chromosome 21. The APP gene is preferentially expressed in the brain cells of the central nervous system. APP mRNA is processed by alternate splicing, and by proteolytic cleavage, such that different isoforms of APP are generated (Pollwein, P. et al. (*Nucl. Acids Res.* 20:63–68 (1992); Price, D. L. et al., *Clin. Neuropharm.* 14:S9–S14 (1991)).

Researchers have proposed that APP is a cell surface receptor or a transmembrane protein, in which the β/A4 domain is partly embedded in the cell membrane. The secretion of the β/A4 peptide thus reflects the cleavage of the domain from the precursor molecule (see, Roch, J. M. et al., *J. Biol. Chem.* 267:2214–2221 (1992)). Although the accumulation of β/A4 peptide in Alzheimer's Disease is believed to result from the so-called "amyloidogenic" processing of one or more of the APP isoforms (Currie, J. R. et al., *J. Neurosci. Res.* 30:687–689 (1991)), the exact mechanism of β/A4 peptide formation is not yet known (see, Johnson, S. A. (In: Review of Biological Research in Aging, Vol. 4., Rothstein, M. (Ed.), Wiley-Liss, NY, 163–170 (1990); Roch, J. M. et al., *J. Biol. Chem.* 267:2214–2221 (1992)).

The deposition of fibrils of β-amyloid peptide in the brain, in the form of neuritic deposits or within the walls of blood vessels, is a characteristic feature of a number of disorders including Alzheimer's Disease, Hereditary Cerebral Hemorrhage With Amyloidosis-Dutch type ("HCHWA-D"), Down's syndrome and cerebral amyloid angiopathy ("CAA"). β-amyloid deposition also occurs in normal aging (Glenner, G. G. et al., *Biochem. Biophys. Res. Commun.* 120:885–890 (1984); Masters, C. L. et al., *Proc. Natl. Acad. Sci. (U.S.A.)* 82:4245–4249 (1985); van Duinen, S. G. et al., *Proc. Natl. Acad. Sci. (U.S.A.)* 84:5991–5994 (1987); Coria, F. et al., *Amer. J. Pathol.* 129:422–428 (1987); Prelli, F. et al., *J. Neurochem.* 51:648–651 (1988)). In CAA and especially in HCHWA-D, where the amyloid deposits are predominantly in the blood vessels, brain hemorrhage is a frequent event (Vonsattel, J. P. G. et al., *Annls. Neurol.* 30:637–649 (1991)).

To date there is no treatment for Alzheimer's Disease at any stage of its development. Two therapeutic reagents, Cognex and Menthane, appear to give slight relief to some victims but do not alter the course of the disease.

In view of the importance of diagnosing, predicting, and treating Alzheimer's Disease, an effective means for achieving these goals would be highly desirable. It would further be desirable to provide an improved thrombolytic therapy that would prevent or lessen the risk of undesired hemorrhage. The present invention provides reagents and methods for accomplishing such improved diagnosis and therapy.

SUMMARY OF THE INVENTION

Figure 1:
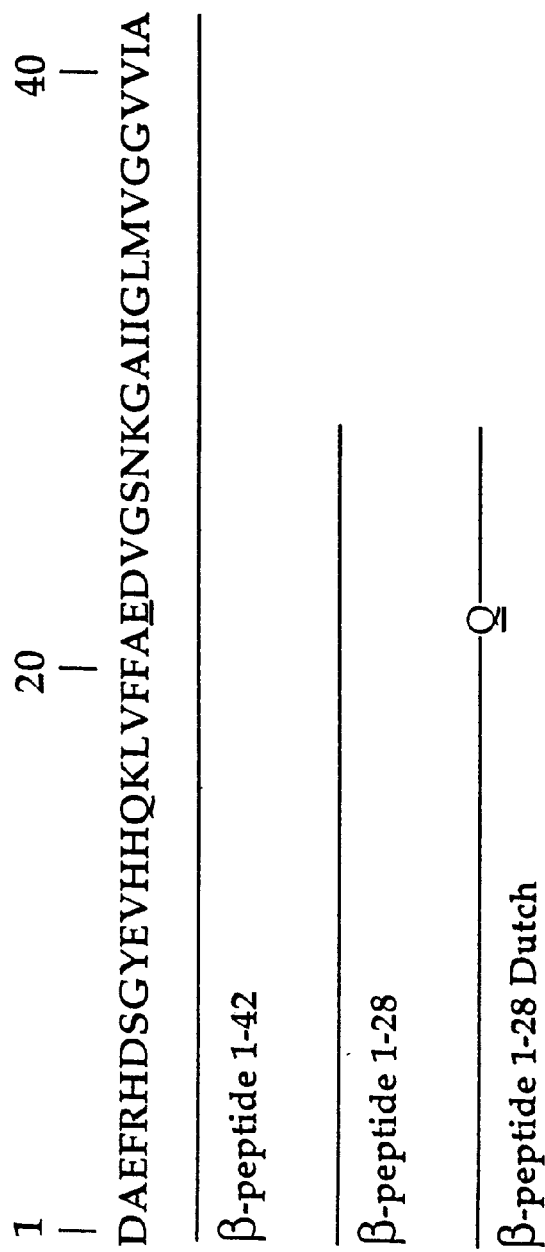
FIG. 1 provides the amino acid sequences of synthetic β-amyloid peptides: β-amyloid peptide 1–42, (β-amyloid peptide 1–28 and β-amyloid peptide 1–28 Dutch, the variant found in HCHWA-D. Residue 22, which corresponds to the mutation in the HCHWA-D peptide, is underlined.

The invention relates to an improved method for preventing or treating vascular hemorrhaging such as that incident to thrombolytic therapy. More specifically, the invention concerns methods for providing improved thrombolytic therapy to individuals who receive such therapy, and for diagnosing and treating diseases, such as Alzheimer's Disease, that are characterized by the deposition of amyloid peptide.

In detail, the invention provides a method for preventing or treating potential vascular hemorrhaging, or Alzheimer's Disease, in an individual, especially hemorrhaging incident to the administration of a thrombolytic agent to an individual suffering from acute cardiovascular disease, which comprises administering to the individual an effective amount of an agent that specifically binds to β-amyloid peptide. The invention particularly concerns the embodiment in which the binding of amyloid peptide by the agent prevents the amyloid peptide from interacting with a thrombolytic agent.

The invention also concerns the embodiments of this method wherein the agent that specifically binds to β-amyloid peptide is an antagonist of β-amyloid binding by the thrombolytic agent, wherein the thrombolytic agent is tissue plasminogen activator or streptokinase, and wherein the acute cardiovascular disease is caused by undesired thrombus production (such as, for example, myocardial infarction, stroke, ischemia, and pulmonary embolism).

The invention particularly concerns the embodiments wherein the agent is an antibody, or an antibody derivative, that binds β-amyloid peptide or fibrils containing β-amyloid peptide but does not block fibrin's ability to bind and stimulate the thrombolytic agent (e.g., tissue plasminogen activator).

The invention also provides a method for providing thrombolytic therapy, and of preventing or treating potential vascular hemorrhaging, which comprises administering to the individual an effective amount of a mutant derivative of t-PA, wherein the derivative specifically binds to fibrin, but is substantially incapable of binding to β-amyloid peptide.

The invention also provides a method for preventing or treating potential neuronal damage (such as neuron degeneration or nerve cell death, and in particular, the neuronal damage characteristic of Alzheimer's Disease), which comprises providing an antagonist of tissue plasminogen activator (i.e., an inhibitor of t-PA action, a repressor of t-PA expression, an anti-t-PA antibody, etc.) to nerve cells in an amount sufficient to provide such cells with an effective concentration of t-PA that is within the beneficial range at which t-PA is in contact with the nerve cells of individuals who do not suffer from such neuronal damage.

The invention additionally provides a method for diagnosing the presence of amyloid plaques in an individual which comprises administering to the individual a labeled agent that specifically binds to a β-amyloid peptide, in an amount sufficient to permit the detection of any of the β-amyloid peptide that binds to the agent, wherein the agent is selected from the group consisting of (1) a tissue plasminogen activator analog that binds to β-amyloid peptide, but does not bind to fibrin (2) an antibody, or an antibody derivative, that binds β-amyloid peptide but does not bind fibrin.

The invention additionally provides a method for diagnosing the presence of amyloid peptides in an individual which comprises incubating material (such as, for example, cerebrospinal fluid, urine, tissue samples, etc.) obtained from the individual with a labeled agent that specifically binds to β-amyloid peptide, in an amount sufficient to permit the detection of any of the β-amyloid peptide that binds to the agent, wherein the agent is selected from the group consisting of (1) a tissue plasminogen activator analog that binds to β-amyloid peptide, but does not bind to fibrin (2) an antibody, or an antibody derivative, that binds β-amyloid peptide but does not bind fibrin.

The invention also provides a method for diagnosing the presence of β-amyloid peptides in a individual which comprises incubating material obtained from the individual with tissue plasminogen activator, plasminogen and a plasmin substrate, and determining the extent to which a component of the material stimulates the tissue plasminogen activator to convert the plasminogen to plasmin, wherein the determination is accomplished by measuring either the change in concentration of the plasmin substrate, or the change in concentration of a product of reaction between the plasmin and the plasmin substrate.

The invention is based in part upon the recognition that the progress of Alzheimer's Disease is accelerated in the presence of an imbalance in t-PA concentration in effective contact with nerve cells. As used herein, the term "concentration in effective contact" is intended to refer to the local concentration of a reagent at nerve cells, in contrast to the overall concentration of the agent in bodily fluids. In one embodiment, the present invention thus provides a method for preventing or treating Alzheimer's Disease in an individual whose t-PA concentration in effective contact with nerve cells is deficient (relative to an individual who does not suffer from Alzheimer's Disease) which comprises administering an effective amount of tissue-plasminogen activator to such nerve cells, optionally with plasminogen. In an alternate embodiment, the present invention provides a method for preventing or treating Alzheimer's Disease in an individual whose t-PA concentration in effective contact with nerve cells is in excess (relative to an individual who does not suffer from Alzheimer's Disease), which comprises administering an effective amount of an antagonist of tissue-plasminogen activator to such nerve cells.

The invention also provides a method for preventing or treating Alzheimer's Disease in an individual whose t-PA concentration in effective contact with nerve cells is deficient (relative to an individual who does not suffer from Alzheimer's Disease) which comprises providing a genetic therapy to the brain cells of the individual, the genetic therapy comprising the administration of a vector that directs the expression and secretion of tissue-plasminogen activator into the cerebrospinal fluid of the individual, optionally with plasminogen.

The invention also provides a method for preventing or treating Alzheimer's Disease in an individual whose t-PA concentration in effective contact with nerve cells is in excess (relative to an individual who does not suffer from Alzheimer's Disease) which comprises providing a genetic therapy to the brain cells of the individual, the genetic therapy comprising the administration of a vector that directs the expression and secretion of an inhibitor of tissue-plasminogen activator into the cerebrospinal fluid of the individual.

The invention also provides a method for preventing or treating Alzheimer's Disease in an individual whose t-PA concentration in effective contact with nerve cells is deficient (relative to an individual who does not suffer from Alzheimer's Disease) which comprises providing an activator of transcription to the brain cells of the individual, wherein the activator is sufficient to mediate the enhanced expression of t-PA by the brain cells.

The invention particularly provides the embodiment of such a method which additionally comprises:

(A) providing a second activator of transcription to the brain cells of the individual, wherein the second activator is sufficient to mediate the expression of plasminogen by the brain cells; or (B) providing plasminogen to the brain cells of the individual.

The invention also provides a method of preventing or treating nerve growth inhibition or nerve cell degeneration which comprises providing to the nerve cells of an individual an effective amount of a thrombin antagonist (such as an anti-thrombin antibody) which inhibits the activity of thrombin or a tissue plasminogen activator antagonist (such as an anti-t-PA antibody) which inhibits the activity of t-PA in the brain or prevents the binding of thrombin or of t-PA to amyloid peptide or to fibrils containing amyloid peptides.

The invention also provides a method for preventing or treating Alzheimer's Disease in an individual whose t-PA concentration in effective contact with nerve cells is in excess (relative to an individual who does not suffer from Alzheimer's Disease) which comprises providing a repressor of transcription to the brain cells of the individual, wherein the repressor is sufficient to mediate the repression of t-PA expression by the brain cells.

DESCRIPTION OF THE PREFERRED EMBODIMENTS

I. Overview of the Invention

Tissue-type plasminogen activator ("t-PA") is the major human plasminogen activator involved in vascular fibrinolysis. As stated above, despite the thrombolytic benefits of t-PA administration in the treatment of acute cardiovascular disease, such administration has resulted in a high incidence of intracranial hemorrhage. Indeed, initial reports of the TIMI-94 and GUSTO-IIA trials of the efficacy of t-PA therapy have demonstrated intracranial bleeding rates equal to or greater than 0.5% (Sobel, B. E., *Circulation* 90:2147–2152 (1994)). The cause of such bleeding has not been previously recognized. However, as discussed by Sobel, B. E., factors such as hypertension, age, female gender, impaired liver function, vitamin K levels, aspirin usage, β-blocker usage, or nitrate usage have been proposed as factors (Sobel, B. E., *Circulation* 90:2147–2152 (1994)). Bleeding has been attributed to the susceptability of the cerebral vasculature in specific patients, including those with occult amyloid deposition in vessel walls, to injury by proteolytic agents such as plasmin (Sobel, B. E., *Circulation* 90:2147–2152 (1994)). Although a relationship between intracranial hemorrhaging and amyloid deposit presence has been suggested, the causal relationship between amyloid deposits and hemorrhaging, and a means for circumventing this relationship has not previously been identified (Pendlebury, W. W. et al., Annl. Neourol. 29:210–213 (1991); Ishii, N, et al., J. Neurol. Neurosurg. Psychiat. 47:1203–1210 (1984); Kase, C. S. et al., Ann. Intern. Med. 112:17–21 (1990); Wijdicks, E. F. M. et al., Stroke 24:554–557 (1993)).

The present invention derives, in part, from the recognition that the β-amyloid peptide is the cause of the reported intracranial bleeding, and mediates such vascular and cellular damage by interacting with, and stimulating, tissue plasminogen activator or streptokinase to produce plasmin. The presence of plasmin catalyzes proteolysis and rupture of vessel walls at the site of the amyloid deposit.

Thus, agents which suppress this interaction may be used therapeutically to attenuate or prevent the vascular damage caused by amyloid deposits. One aspect of the present invention thus concerns agents and methods for preventing hemorrhaging, especially hemorrhaging that may occur due to the administration of thrombolytic agents such as t-PA or streptokinase.

A mechanism for the involvement of amyloid peptide in the progression of Alzheimer's Disease is discussed by Selkoe, D. J. (Trends Neurol. Sci. 16:403–409 (1993), herein incorporated by reference). Additionally, thrombin deposits have been found to accumulate in the brains of patients with Alzheimer's Disease (Akiyama, H. et al., Neurosci. Lett. 146:152–154 (1992); Akiyama, H. et al., Neurobiol. Aging 15:S124 (1994)). Within the brain, thrombin appears to function as a nerve growth inhibitor, causing neurons to retract their neurites (Cunningham, D. D., Annl. N.Y. Acad. Sci. 674:228–236 (1992);Gurwitz, D. et al., Proc. Natl. Acad. Sci. (U.S.A.) 85:3440–3444 (1988)). Recently, a number of low-density lipoprotein receptor ("LRP")-binding proteins, including t-PA, have been found in amyloid plaque deposits (Rebeck, G. W. et al., Neurobiol. Aging 15:S117 (1994)).

One aspect of the present invention concerns the recognition that thrombin-mediated nerve growth inhibition occurs through the accumulation of thrombin at the site of amyloid deposits. Thus, thrombin antagonists, such as antithrombin or anti-amyloid antibodies or β-amyloid peptidomimetic agents, which can prevent or inhibit thrombin-amyloid peptide association, can be used to prevent or treat neurological disorders.

The capacity of β/A4-amyloid peptide to activate t-PA also provides a highly sensitive method for diagnosing the presence of the β/A4-amyloid peptide. Similarly, agents that stimulate t-PA synthesis (for example, in the brain) can be used to induce the plasmin-mediated dissolution of amyloid deposits.

Thus, in one embodiment, the present invention provides an improved therapy for thrombolytic intervention in the case of cardiovascular disease, as well as a diagnostic and therapeutic approach to the management of Alzheimer's Disease.

II. The Interrelationship Between Amyloid Deposits and t-PA

The main component of the amyloid deposit is a 39–43 amino acid peptide with a molecular weight of approximately 4,200 D that is derived from the much larger membrane-bound β-amyloid precursor protein (APP) (Kang, J. et al., Nature 325:733–736 (1987); Robakis, N. K. et al., Proc. Natl. Acad. Sci (U.S.A.) 84:4190–4194 (1987)). In HCHWA-D, the β-amyloid peptide has a glutamic acid to glutamine substitution at position 22 (Levy, E. et al., Science 248:1124–1126 (1990)). Although Alzheimer's Disease and HCHWA-D are both characterized by β-amyloid deposition, the two diseases differ in the major sites at which β-amyloid deposition occurs. In Alzheimer's Disease β-amyloid deposits are found predominantly in cerebral cortex, but in most cases there is also some degree of amyloid deposition in the walls of cerebral vessels (Tomlinson, B. E., In: Greenfield's Neuropathology, 5th edition (eds. Adams, J. H. & Duchen, L. W.), 1284–1410 (Edward Arnold, London. 1992)). Clinically, Alzheimer's Disease is characterized by progressive dementia.

In HCHWA-D β-amyloid is predominantly found in the walls of small and medium sized vessels of the leptomeninges and the cerebral cortex and in parenchymal deposits that resemble the early preamyloid deposits of Alzheimer's Disease (van Duinen, S. G. et al., Proc. Natl. Acad. Sci (U.S.A.) 84:5991–5994 (1987); Giaccone, G. et al., Neurosci. Lett. 97: 232–235 (1989). Patients with HCHWA-D develop recurrent hemorrhages which are ultimately fatal (Wattendorf, A. R. et al., J. Neurol. Sci. 55:121–135 (1982); Luyendijk, W. et al., J. Neurol. Sci. 85:267–280 (1988)). In both of these diseases and in other conditions giving rise to cerebral amyloid angiopathy, the β-amyloid found in blood vessel walls appears to accumulate within the tunica adventitia and the tunica media of the muscle layer (Tomlinson, B. E., In: Greenfield's Neuropathology, 5th edition (eds. Adams, J. H. & Duchen, L. W.), 1284–1410 (Edward Arnold, London. 1992); Vinters, H. V., Stroke 18:311–324 (1987)). However, fibrils may first be formed closer to the vessel lumen, within the abluminal vascular basement membrane (Yamaguchi, H. et al., Amer. J. Pathol. 141:249–259 (1992)).

The origin of β-amyloid in both Alzheimer's Disease and HCHWA-D has not been clearly established but it has been proposed that the vascular system is one source of APP (Tagliavini, F. et al., Lab. Investigation 62:761–767 (1990); Selkoe, D. J., Neurobiol. Aging 10:387–395 (1989)). The amyloid precursor may first pass through the endothelium to be deposited within the vessel musculature. This mechanism is supported by the frequent finding of many serum proteins in vessel walls affected by CAA, suggesting that the microvasculature exhibits a relatively non-specific leakiness to some macromolecules (Powers, J. M. et al., J. Neuropathol. Exper. Neurol. 40:592–612 (1981); Goust, J. M. et al., J. Neuropathol. Exper. Neurol. 43:481–488 (1984)).

Human tissue-type plasminogen activator (t-PA) is a major extrinsic thrombolytic agent, originating from the vascular endothelium. Plasminogen activation by t-PA is stimulated by fibrinogen, and more dramatically by fibrin and fibrin analogs (Holyaerts, M. et al., J Biol. Chem. 259:2912–2919 (1982)).

The discovery that β-amyloid peptides function as fibrin or fibrinogen mimics that stimulate t-PA is consistent with observations that anti-β-amyloid peptide antibodies cross-react with conformational epitopes on human fibrinogen and that anti-fibrinogen antibodies cross-react with β-amyloid peptide (Stem, R. A. et al., FEBS Letters 264: 43–47 (1990)). The t-PA-β-amyloid interaction causes amyloid peptide fibrils in blood vessel walls to promote high local concentrations of t-PA and consequently high local concentrations of plasmin which result in proteolysis, rupture, and hemorrhaging of vessel walls.

III. The Prevention or Treatment of Vascular Hemorrhaging Incident to Thrombolytic Therapy A central aspect of the present invention concerns the recognition that the undesired hemorrhaging which is observed in some individuals receiving thrombolytic therapy (especially t-PA) is caused by the presence of β-amyloid deposits which stimulate the ability of the administered t-PA to produce plasmin at the site of the deposit.

Such undesired stimulation of t-PA can be attenuated or prevented by providing the patient with an effective amount of an agent that can specifically bind to the β-amyloid peptide or its fibrils. Most preferably, the agent will be selected such that it is incapable or substantially incapable of binding fibrin.

The term "specific binding," as used herein refers to the capacity of two or more molecules to bind together due to structural attributes of each molecule. A molecule is said to be capable of "specific binding" to another molecule if such binding is dependent upon the respective structures of the molecules. The term is intended to distinguish such binding from non-specific binding that occurs without regard to the particular structures of the molecules involved (e.g., the binding of proteins to nitrocellulose is an example of non-specific binding). Examples of specific binding include the binding of an antibody to its antigen, the binding of a hormone to its receptor, etc. A molecule is substantially incapable of binding to another molecule where the extent, if any, of such binding fails to cause a physiologically relevant change in the concentration or activity of the unbound agents. Most preferably, the molecules of the present invention will exhibit "highly specific binding," such that they will be incapable or substantially incapable of binding to closely related molecules.

As used herein, vascular hemorrhaging is said to be prevented by the administration of an agent when such administration decreases the probability of hemorrhage in that patient relative to the probability of hemorrhage in patients who have not received that agent. Such administration may be either "prophylactic" or "therapeutic." A prophylactic treatment is one that is provided in advance of any symptom of hemorrhage in order to prevent or attenuate any subsequent hemorrhage. A therapeutic treatment is one that is provided in response to the detection of hemorrhage, and serves to attenuate the degree, extent, or severity of such hemorrhaging. An amount of a therapeutic agent is said to be an "effective amount" if it is sufficient to mediate a clinically significant change in the severity of a symptom, or a clinically significant delay in the onset of a symptom.

In some embodiments, the molecules of the present invention may be used in a "purified" form. As used herein, a molecule is said to be in a "purified" form if it is present in a preparation that lacks a molecule that is normally associated with that molecule in its natural state.

The preferred binding agents of the present invention are antibodies or antibody fragments. Such antibodies may be intact immunoglobulins, or may be antibody fragments (F(ab'), F(ab')$_2$, single chain antibodies, etc.), recombinant antibodies, antibody fusion proteins, chimeric antibodies, etc. Such molecules may be obtained by screening among antibodies elicited in response to immunization with either a β-amyloid peptide or a peptide or peptidomimetic molecule that is a "functional analog" of a β-amyloid peptide.

As used herein, the term "functional analog" includes both "classical analogs" and "mimetic analogs." A classical analog of a molecule is one that has a similar biological activity, and is chemically related to the molecule. By way of illustration, a non-naturally occurring mutant of t-PA would comprise a classical analog of t-PA. Similarly, a mutated β/A4-amyloid peptide would comprise an example of a classical analog of the β/A4-amyloid peptide Likewise, an molecule isolated from a non-human mammalian species (such as a mouse, monkey, etc.) would comprise an example of a classical analog of that molecule. In contrast, a "mimetic analog" of a molecule retains the biological activity of the molecule, but is unrelated chemically. A peptidomimetic molecule whose structure mimics a binding site of t-PA or of β/A4-amyloid peptide would comprise a "mimetic analog" of such peptides.

The amino acid sequence of the β/A4-amyloid peptide is shown as SEQ ID NO:1. Preferred biologically active fragments of the β/A4-amyloid peptide lack amino acid residues 29–42 of SEQ ID NO:1. The fragments may be composed of only those amino acid residues present in SEQ ID NO:1, or may contain deletions, insertions, additions or substitutions of one, two or more amino acids from either terminus, or from an internal site. Examples of such fragments include a peptide comprising SEQ ID NO:1 residues 1–28, and a peptide comprising SEQ ID NO:1 residues 1–28, wherein the amino acid at residue 22 (Glu) is replaced with Gln.

SEQ ID NO:1 Asp Ala Glu Phe Arg His Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala

Additional t-PA or antibody binding fragments may be readily identified. Such molecules may be fractionated from the β/A4-amyloid peptide by proteases, cyanogen bromide, etc. and the resultant fragments assessed for their capacity to specifically bind and/or activate t-PA. More preferably, however, such fragments may be identified through the use of Epitope Scanning™ strategy (Cambridge Research Biochemicals, Inc.). Thus, the linear sequence of amino acids of the β/A4-amyloid peptide is evaluated to define a set of fragments of predefined length which overlap other members of the set by a preselected number of residues. The predefined peptide length may be any number. However, it is preferred that the length be great enough to confer some amount of secondary structure to the peptide, and to be small enough that the entire library of peptides can be synthesized. Thus, lengths of from about 6 to about 25 amino acids are preferred. In selecting the predefined length, a general consideration is that 90% of linear epitopes recognized by antibodies are six amino acids or less in length (Geysen, H. M. et al., *Proc. Natl. acad. Sci. (U.S.A.)* 81:3998–4002 (1984)). The preselected extent of overlap will generally exceed 50%, and will preferably be selected such that the overlap will be from about (n−1) to (n−3), where "n" is the predefined peptide length. An overlap of (n−1) is particularly preferred.

Once the sequences of the entire library of peptide fragments have been ascertained, the peptides are synthesized, preferably using automated synthesizers such as a multipin peptide synthesis system. Suitable systems or peptide synthesis services are available from Cambridge Research Biochemicals, Inc.; ICI Biological Products, Inc.; Chiron Mimitopes, Inc.; Lab Products International, Ltd.

In order to identify peptides having desired determinants, each peptide is introduced into a well of a microtiter plate, and evaluated for its capacity to bind and/or activate t-PA. Such determinations may be made in any of a variety of ways. Preferably, the effects of such peptides on the conversion of plasminogen to plasmin by t-PA are determined using a spectrophotometric method that permits the determination of the apparent first-order rate constant of plasminogen activation.

In one embodiment, the peptide is immobilized to the well surface, and the assay is conducted by determining the extent of antibody that becomes immobilized to the support. More preferably, a competitive ELISA is conducted in which the ability of the peptide to compete with β-amyloid peptide antigen binding to antisera is determined. The extent of antibody binding by each peptide is determined and used to map the antigenic determinants of the molecule. Where no determinants are observed, the method is repeated using peptides of greater predefined length. When all observed determinants are present in only a single fragment, the method may be repeated using peptides of lesser predefined length. In such manner, the library of peptides is evaluated and members containing the antigenic determinants are identified.

Once a particular peptide has been found to have an immunological determinant, the peptide can be used to elicit antibody production in naive animals (i.e., animals that have not been previously exposed to human β-amyloid peptide). Where desired, the peptides can be modified to increase their immunogenicity. Thus, they may be modified to contain an amino-terminal and/or a carboxyl-terminal cysteine or lysine residue with or without spacer arms. The peptides may be conjugated to carriers such as bovine serum albumin, ovalbumin, human serum albumin, KLH (keyhole limpet hemocyanin), or tetanus toxoid. The use of human serum albumin is preferred over ovalbumin or bovine serum albumin, since it causes lower background levels in ELISAs and dot blots than do the albumins of other species.

Since the administration of t-PA to dissolve dots of individuals suffering or recovering from acute cardiovascular disease occurs over a brief and discrete time period (generally ranging from a few hours to a few days), non-human origin antibodies may be used. Thus, polyclonal antibodies of non-human animals that bind to β-amyloid peptides may be administered in accordance with the methods of the present invention, irrespective of any anti-idiotypic or anti-heterologous immune reaction that may occur. Suitable polyclonal antibodies may be prepared, for example, by immunizing female rabbits or castrated male sheep with 50 to 500 μg of a β-amyloid peptide preparation. The immunogen is preferably suspended in water and emulsified with Freund's Complete Adjuvant prior to injection. Animals may be injected in multiple intradermal sites (preferably subcapsularly) and are preferably boosted after 4 weeks with β-amyloid peptide (in Freund's Incomplete Adjuvant) at one half the amount of peptide used for the initial immunization. If desired, additional boosts at monthly intervals using Freund's Complete Adjuvant may be given to obtain even higher antibody titers.

In this embodiment of the invention, adverse immune responses are not relevant to the treatment provided by the antibodies since the duration of treatment is of the same or lower order of magnitude than the time needed for the patient to clear the foreign origin antibodies. To the extent that such undesired immune reaction occurs, the number of doses or the amount of each dose is increased to compensate.

Although polyclonal antibodies can be used, murine monoclonal antibodies are particularly preferred (Koprowski, H. et al., U.S. Pat. Nos. 4,172,124 and 4,196, 265). BALB/c mice are preferred for this purpose, however, equivalent strains may also be used. The animals are preferably immunized with approximately 25 μg of affinity purified β-amyloid peptide (or an equivalent thereof) that has been emulsified with a suitable adjuvant (such as Titer-Max adjuvant (Vaxcel, Norcross, Ga.)). Immunization is preferably conducted at two intramuscular sites, one intraperitoneal site, and one subcutaneous site at the base of the tail. An additional i.v. injection of approximately 25 μg of antigen is preferably given in normal saline three weeks later. After approximately 11 days following the second injection, the mice may be bled and the blood screened for the presence of anti-β-amyloid antibodies. Preferably, a direct binding ELISA is employed for this purpose.

Most preferably, the mouse having the highest antibody titer is given a third i.v. injection of approximately 25 μg of β-amyloid peptide or fragment. The splenic leukocytes from this animal may be recovered 3 days later, and are then permitted to fuse, most preferably, using polyethylene glycol, with cells of a suitable myeloma cell line (such as, for example, the P3×63Ag8.653 myeloma cell line). Hybridoma cells are selected by culturing the cells under "HAT" (hypoxanthine-aminopterin-thymine) selection for about one week. The resulting hybridoma clones may then be screened for their capacity to produce monoclonal antibodies ("mAbs") to β-amyloid peptide, preferably by direct ELISA.

Thus, in another embodiment, this invention contemplates a novel continuous hybridoma cell line which expresses monoclonal anti-β-amyloid peptide antibody, as well as the use of such cell line to produce such antibody. The present invention also contemplates a novel continuous hybridoma cell line which expresses anti-β-amyloid peptide antibody obtained by immunizing an animal with β-amyloid peptide. Antibody may be obtained through the in vitro culturing of the cells, or by injecting the cells into a histocompatable animal where they can proliferate and produce high levels of anti-β-amyloid peptide antibody. Such antibody can be recovered from the animal's ascites fluid, lymph, blood, etc.

In a highly preferred embodiment, populations of polyclonal β-amyloid peptide antibodies, or species of monoclonal β-amyloid peptide antibodies, are further screened to remove those antibodies that are additionally capable of specifically binding to fibrin. In the case of polyclonal sera, such removal can readily be accomplished by passing the sera through a column containing immobilized fibrin. In the case of monoclonal antibodies, such removal can be accomplished by evaluating the capacity of the molecule to bind fibrin, and then discarding those hybridomas that produce antibodies that specifically bind both β-amyloid peptide and fibrin. The elimination of antibodies that bind fibrin serves to ensure that the antibodies will not disrupt the desired ability of the administered t-PA to dissolve fibrin clots.

Where chronic or prolonged administration is desired, the use of non-immunogenic antibodies is preferred. Such molecules can be pseudo-homologous (i.e., produced by a non-human species, but altered to a form that is immunologically indistinct from human antibodies). Examples of such pseudo-homologous molecules include "humanized" (i.e., non-immunogenic in a human) antibodies prepared by recombinant or other technology. Such antibodies are the equivalents of the monoclonal and polyclonal antibodies, but are less immunogenic, and are better tolerated by the patient.

Humanized antibodies may be produced, for example, by replacing an immunogenic portion of an antibody with a corresponding, but non-immunogenic portion (i.e., chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc.*

Res. 47:999–1005 (1987); Wood, C. R. et al., *Nature* 314:446–449 (1985)); Shaw et al., *J. Natl.Cancer Inst.* 80:1553–1559 (1988); all of which references are incorporated herein by reference). General reviews of "humanized" chimeric antibodies are provided by Morrison, S. L. (*Science,* 229:1202–1207 (1985)) and by Oi, V. T. et al., *BioTechniques* 4:214 (1986); which references are incorporated herein by reference).

Suitable "humanized" antibodies can alternatively be produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988); all of which references are incorporated herein by reference).

In an alternate embodiment of the invention, a mutant derivative of t-PA may be administered in order to achieve a more desirable thrombolytic therapy. Preferably, such a t-PA derivative will retain an ability to bind to fibrin, but will be substantially or completely incapable of binding to amyloid peptides of amyloid deposits. Such t-PA mutants may be obtained by, for example, mutating a nucleic acid molecule that encodes t-PA, expressing such molecules in a mammalian host cell line (e.g., Chinese hamster ovary cells), and determining whether such mutagenesis has resulted in a t-PA variant which can bind to fibrin, but which has a decreased ability to bind to amyloid peptide.

IV. The Diagnosis of Alzheimer's Disease and Related Conditions

A second aspect of the present invention is derived, in part, from the recognition that the amyloid peptide of Alzheimer's Disease and HCHWA-D stimulate t-PA to cleave plasminogen into fibrin. Thus, the present invention provides a means for diagnosing the presence of amyloid peptide associated with brain (i.e., "CNS" or central nervous system) cells of a patient. As used herein, a "CNS cell" is a neuron, or a cell in contact with nerve cells, such as a glial cell.

In one embodiment, such diagnosis is conducted in vivo, by imaging the location and extent of amyloid peptide deposit. In accordance with this embodiment of the invention, an analog of t-PA is provided to an individual, and its binding to amyloid deposits is monitored. Most preferably, such t-PA analogs will lack the capacity to bind to fibrin, or to activate plasminogen, but will retain t-PA's capacity to bind amyloid peptide.

Such derivatives can be readily isolated by mutating (or synthesizing) t-PA molecules that are substantially incapable of activating plasminogen (e.g., the t-PA variant in which the serine residue at position 478 has been replaced with an alanine residue), and then screening such molecules for those capable of binding to β-amyloid peptides. The use of such molecules in vivo has the advantage that their administration will not comprise an undesired thrombolytic therapy.

Alternatively, the above-described antibodies to β-amyloid peptides may be used for such diagnosis. Most preferably, such antibodies will be capable of binding to β-amyloid peptides but be substantially incapable of binding to fibrin.

Most preferably, for such in vivo use, such molecules will be detectably labeled, as with radioisotopes, paramagnetic labels, etc. so as to facilitate the imaging of the location of any amyloid deposit.

In yet another embodiment, material (such as blood, sera, urine, cerebrospinal fluid, tissue biopsies, etc.) may be withdrawn from a patient and evaluated for the presence of amyloid peptide using the above-described anti-β-amyloid peptide antibodies or t-PA analogs. The detection of these molecules may be done by any of a variety of methods. In one embodiment, antibodies are employed that are capable of binding to the β-amyloid peptides, and the presence of such molecules is determined via an immunoassay. A large number of suitable immunoassay formats have been described (Yolken, R. H., *Rev. Infect. Dis.* 4:35 (1982); Collins, W. P., In: *Alternative Immunoassays,* John Wiley & Sons, NY (1985); Ngo, T. T. et al., In: *Enzyme Mediated Immunoassay,* Plenum Press, NY (1985); incorporated by reference herein.

The simplest immunoassay involves merely incubating an anti-β-amyloid peptide antibody with a sample suspected to contain the target β-amyloid peptide molecule. The presence of the target molecule is determined by the presence, and proportional to the concentration, of any antibody bound to the target molecule. In order to facilitate the separation of target-bound antibody from the unbound antibody initially present, a solid phase is typically employed. Thus, for example the sample can be passively bound to a solid support, and, after incubation with the antibody, the support can be washed to remove any unbound antibody.

In more sophisticated immunoassays, the concentration of the target molecule is determined by binding the antibody to a support, and then permitting the support to be in contact with a sample suspected to contain the target molecule. Target molecules that have become bound to the immobilized antibody can be detected in any of a variety of ways. For example, the support can be incubated in the presence of a labeled, second antibody that is capable of binding to a second epitope of the target molecule. Immobilization of the labeled antibody on the support thus requires the presence of the target, and is proportional to the concentration of the target in the sample. In an alternative assay, the target is incubated with the sample and with a known amount of labeled target. The presence of any target molecules in the sample competes with the labeled target molecules for antibody binding sites. Thus, the amount of labeled target molecule that is able to bind the antibody is inversely proportional to the concentration of target molecule in the sample.

As indicated above, immunoassay formats may employ labeled antibodies to facilitate detection. Radioisotopic immunoassays ("RIAs") have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. RIAs are described in *Laboratory Techniques and Biochemistry in Molecular Biology,* by Work, T. S., et al., North Holland Publishing Company, NY (1978), with particular reference to the chapter entitled "An Introduction to Radioimmune Assay and Related Techniques" by Chard, T., incorporated by reference herein.

Enzyme-based immunoassay formats (ELISAs) have the advantage that they can be conducted using inexpensive equipment, and with a myriad of different enzymes, such that a large number of detection strategies—colorimetric, pH, gas evolution, etc.—can be used to quantitate the assay. In addition, the enzyme reagents have relatively long shelf-lives, and lack the risk of radiation contamination that attends to RIA use. ELISAs are described in *ELISA and Other Solid Phase Immunoassays* (Kemeny, D. M. et al., Eds.), John Wiley & Sons, NY (1988), incorporated by reference herein. For these reasons, enzyme labels are particularly preferred.

No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Examples of suitable enzymes include peroxidase, acetylcholine esterase, alpha-glycerol phosphate dehydrogenase, alkaline phosphatase, asparaginase, β-galactosidase, catalase, delta-5-steroid isomerase, glucose oxidase, glucose-6-phosphate dehydrogenase, glucoamylase, glycoamylase, luciferase, malate dehydrogenase, peroxidase, ribonuclease, staphylococcal nuclease, triose phosphate isomerase, urease, yeast-alcohol dehydrogenase, etc. Peroxidase and urease are among the more preferred enzyme labels, particularly because of chromogenic pH indicators which make its activity readily visible to the naked eye.

In lieu of such enzyme labels, chemiluminescent, radioisotopic, or fluorescent labels may be employed. Examples of suitable radioisotopic labels include $^{3}H$, $^{111}In$, $^{125}I$, $^{131}I$, $^{32}p$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}pb$, $^{47}Sc$, $^{109}Pd$, etc. Examples of suitable chemiluminescent labels include luminal labels, isoluminal labels, aromatic acridinium ester labels, imidazole labels, acridinium salt labels, oxalate ester labels, luciferin labels, aequorin labels, etc. Examples of suitable fluorescent labels include fluorescein labels, isothiocyanate labels, rhodamine labels, phycoerythrin labels, phycocyanin labels, allophycocyanin labels, o-phthaldehyde labels, fluorescamine labels, etc. For purposes of magnetic resonance imaging, paramagnetic labels ($^{3}H$, $^{13}C$, etc.) are preferred.

V. The Prevention or Treatment of Alzheimer's Disease and Related Conditions

Yet another aspect of the present invention concerns the prevention or treatment of Alzheimer's Disease and related conditions.

As indicated, the HCHWA-D condition reflects both the deposition of amyloid peptide on to the surfaces of blood vessels, and the proteolysis of such deposits by plasmin, in a t-PA dependent process. In accordance with the methods of the present invention, Alzheimer's Disease may be treated by a plasmin-mediated proteolysis of the β-amyloid peptides of the Alzheimer's amyloid plaque deposits. Such proteolysis does not occur naturally in Alzheimer's Disease victims because the gene encoding t-PA is not highly expressed in the brain, the site of the Alzheimer's Disease deposits.

Thus, in accordance with one embodiment of the present invention, the administration of t-PA to nerve cells comprises a therapy for Alzheimer's Disease.

Alternatively, agents which induce the synthesis of t-PA may be provided to patients in order to prevent or treat Alzheimer's Disease. A preferred agent is a DNA molecule that encodes t-PA. The general principles of such gene therapy have been discussed by Oldham, R. K. (In: *Principles of Biotherapy, Raven Press, NY,* 1987); Boggs, S. S. (Int. *J. Cell Clon.* 8:80–96 (1990)); Karson, E. M. (*Biol. Reprod.* 42:39–49 (1990)); Ledley, F. D., In: *Biotechnology, A Comprehensive Treatise, volume 7B, Gene Technology,* VCH Publishers, Inc. NY, pp 399–458 (1989)); all of which references are incorporated herein by reference.

In accordance with such a method, DNA molecules that encode t-PA are incorporated into a vector and delivered to brain cells or to other cells which are subsequently implanted into the brain. Recombinant adenovirus is an efficient vector for such in vivo gene transfer. The transcription of the t-PA-encoding DNA can be mediated from any suitable eucaryotic promoter. Examples of such suitable promoters include the RSV LTR, the SV40 early promoter, the cytomegalovirus (CMV) IE promoter, and the MMTV promoter.

In an especially preferred sub-embodiment, the genetic therapy will link the t-PA-encoding DNA to sequences that will direct the secretion of the t-PA into the cerebrospinal fluid. The secretion of therapeutic gene products even from a modest population of transfected cells will create a microenvironment around the amyloid deposits that will contain a high concentration of t-PA.

Although, as indicated above, such gene therapy can be provided to a recipient in order to treat an existing condition, the principles of the present invention can be used to provide a prophylactic gene therapy to individuals, including those who, due to inherited genetic mutations, or somatic cell mutation, are predisposed to Alzheimer's Disease.

A further aspect of the present invention concerns the recognition that the Alzheimer's amyloid β peptide is a potent functional mimic of fibrin, the main protein component of blood clots. As indicated above, tissue plasminogen activator is the body's main defense against spontaneous blood clotting, such as that which occurs in heart attacks and stroke. The mechanism of t-PA action involves its recognition, targeting, and destruction of the fibrin molecules in blot clots.

It has been known for a number of years that the amlyoid β peptide can form deposits in the blood vessels of the brain (cerebral vasculature) as well as in the neuritic plaques associated with Alzheimer's Disease; this condition is known as cerebral amyloid angiopathy or CAA. CAA is a very significant risk factor for brain hemorrhages.

One aspect of the present invention relates to the recognition that too much t-PA can also cause brain hemorrhage. This recognition led to that aspect of the present invention that is concerned with whether the amyloid β peptide, might appear to t-PA as resembling fibrin, and thereby cause t-PA to target and attack amyloid deposits in the cerebral vasculature as if they were fibrin-containing clots—a molecular example of mistaken identity. Because t-PA triggers a powerful cascade of local digestive action, collateral damage from this attack could be responsible for the bursting of the cerebral blood vessels in a brain hemorrhage. One aspect of the present invention thus concerns the recognition that the amyloid β peptide indeed interacts functionally with t-PA. Any of a variety of t-PA antagonists may be employed to modulate or block this effect. Such antagonists include antibodies to t-PA (particularly humanized antibodies) or antibody fragments, t-PA ligands, t-PA analogues that bind amyloid β peptide without causing proteolysis, etc.

The implications of this recognition to the treatment of Alzheimer's Disease are potentially profound. In the brain as well as in the blood t-PA appears to have a dual character. In the blood, the right amount of t-PA removes blood clots and protects the body against heart attacks and strokes; too much t-PA, however, causes hemorrhagic complications. In the brain, the right amount of t-PA allows for the synaptic plasticity that is vital for learning and memory; too much t-PA, however, can cause neurotoxicity. It is possible that amyloid β peptide deposits are toxic to neurons because they attract toxic levels of t-PA to the vicinity of the nerves and trigger neuronal dystrophy. This hypothesis is consisent with what is known regarding the pathology and physiology of neural degeneration in Alzheimer's Disease.

Thus, one aspect of the present invention involves providing neuronal therapy (to, for example, treat or prevent Alzheimer's Disease) by "correcting" the effective concentration of tissue plasminogen activator in contact with the nerve cells of treated individuals. Depending upon whether the treated individual has a deficient or an excess effective concentration of tissue plasminogen activator in contact with his/her nerve cells, such "correction" may entail either increasing t-PA concentration or expression (optionally with additionally administered plasminogen) or providing an antagonist of t-PA activity or expression. It will be understood that such correction is intended to modulate the concentration of tissue plasminogen activator in effective contact with the nerve cells of treated individuals so that it is within a bernficial range encountered in individuals who do not have Alzheimer's Disease.

VI. Administration of the Molecules of the Present Invention

The above-described therapeutic agents of the present invention can be formulated according to known methods used to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in. Remington's Pharmaceutical Sciences (16th ed., Osol, A., Ed., Mack, Easton Pa. (1980)). In order to form a pharmaceutically acceptable composition suitable for effective administration, such compositions will contain an effective amount of such agents, together with a suitable amount of carrier vehicle.

Additional pharmaceutical methods may be employed to control the duration of action. Control release preparations may be achieved through the use of polymers to complex or absorb the agents. The controlled delivery may be exercised by selecting appropriate macromolecules (for example polyesters, polyamino adds, polyvinyl pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled release preparations is to incorporate the agents into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly-(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In a preferred method for treating hemorrhaging, the antibody and other amyloid peptide-binding agents of the present invention are provided concurrently with, or more preferably, prior to, the administration of a thrombolytic agent. Such antibody and other amyloid peptide-binding agents are preferably provided by injection, most preferably by intravenous infusion.

Previously, despite the urgency of acute cardiovascular illness, the hemorrhaging associated with the administration of thrombolytic agents led health providers to avoid providing such agents until the diagnosis of cardiovascular disease had been confirmed by a cardiologist. Since the present invention attenuates a possibility of hemorrhage, it (either alone, or in conjunction with the administration of the thrombolytic agent) may be provided by acute care providers (such as paramedics, emergency room attendants, etc.). Moreover, since no adverse side-effects of anti-amyloid antibodies are known, and since a delay between the administration of the antibodies and the administration of the thrombolytic agent is desirable, the anti-amyloid antibodies of the present invention are particularly suitable for administration by emergency medical personnel in the treament of suspected or potential acute cardiovascular disorders.

Having now generally described the invention, the same will be more readily understood through reference to the following examples which are provided by way of illustration, and are not intended to be limiting of the present invention, unless specified.

EXAMPLE 1

Effects of β-Amyloid Peptide on t-PA Activity

To investigate the effects of β-amyloid on t-PA activity three synthetic peptides were used (FIG. 1). One peptide contained 42 amino acids and corresponded to the full-length β-amyloid peptide (FIG. 1). The other two peptides contained the 28 N-terminal residues of the β-amyloid peptides found in Alzheimer's Disease or in HCHWA-D. The β-amyloid peptides 1–28 and 1–28 (Dutch) were obtained from Chiron Mimetopes Peptide Systems. The β-amyloid peptide 1–42 was obtained from Bachem Biosciences, Inc. The purity of the peptides was established by high performance liquid chromatography and mass spectrometry. Upon storage under specific conditions, all three peptides readily formed fibrils that are characteristic of β-amyloid peptides.

Fibril formation was accomplished by taking the peptides up in water. 10× calcium and magnesium free phosphate buffered saline ("PBS") was added to give a 1×PBS solution (2.7 mM KCl, 1.2 mM $KH_2PO_4$, 138 mM NaCl, 8.1 mM $Na_2HPO_4$). Fibril formation was obtained by adjusting the pH to the theoretical pI of the β-amyloid peptides. The theoretical pI of β-amyloid peptide 1–42 was 4.9; the theoretical pI of β-amyloid peptide 1–28 was 5.6; the theoretical pI of β-amyloid peptide 1–28 (Dutch) was 6.2. The final concentration of peptide was 1 mg/ml. Fibril formation was found to be rapid at a pH dose to the theoretical isoelectric point (pI) of the peptides. Fibrils were observed immediately or within no more than two days at room temperature. Small aliquots of suspended aggregated peptides were adsorbed onto carbon-coated copper grids and stained with 2% (w/v) uranyl acetate. Samples were examined in a JEOL 1200EX electron microscope.

The effects of β-amyloid peptides on the conversion of plasminogen to plasmin by t-PA were studied using a spectrophotometric method that permits the determination of the apparent first-order rate constant of plasminogen activation. The assay provides a simple system for determining catalytic efficiency and for quantifying plasminogen activator levels. It is based on the knowledge that the conversion of plasminogen to plasmin follows Michaelis-Menten kinetics (Wohl, R. et al., *J. Biol. Chem.* 255:2005–2013 (1980)).

The assay continuously measures the conversion of plasminogen to plasmin by monitoring the hydrolysis of the chromogenic substrate N-benzoyl-L-arginine-p-nitroanilide (BAPA) under non-steady state, first order conditions with respect to plasminogen. The $k_{cat}$ of plasmin for BAPA is low. Ideally, the conversion of plasminogen to plasmin, which is a first-order reaction at the concentrations of plasminogen used, is followed for at least one third of the time required for the complete activation of the plasminogen present. This translates in data-collecting times of up to 24 hours, under the experimental conditions used, when the catalytic efficiency constants are in the order of $10^3 \, M^{-1} \, s^{-1}$, as is the case of unstimulated t-PA. A chromogenic substrate with a very slow hydrolysis rate is necessary in order to avoid its depletion or excessive accumulation of absorbance during the time course of the experiment. The apparent first-order rate constant, $k_{(app)}$, of plasminogen conversion to plasmin is obtained from the assay. The apparent catalytic efficiency constant, $k_{cat}/K_m(app)$, can be calculated if the concentration of plasminogen activator in the assay is known.

The results obtained with the assay are in good agreement with values of catalytic efficiency determined under steady state conditions. In cases where the determination of the catalytic efficiency is sufficient, this assay is considerably easier to perform than assays designed to determine $k_{cat}$ and $K_m$; in traditional Michaelis-Menten studies, difficulties arise concerning the solubility of plasminogen at high concentrations and determination of initial velocities for plasmin production. The assay is suitable for kinetic studies of purified plasminogen activators and can also be used for the determination of plasminogen activator activity levels in complex mixtures containing stimulating factors such as β-amyloid peptides.

The assay was performed in calcium-and-magnesium-free phosphate-buffered saline, pH 7.4 (2.7 mM KCl; 138 mM NaCl; 1.2 mM $KH_2PO_4$; 8.1 mM $Na_2HPO_4$), containing 0.01% Tween 80 (polyoxyethylene (80) sorbitan) at 25° C. A typical reaction contained 0.5 nM t-PA (Activase™, Genentech, Inc.), 0.5 μM human glu-plasminogen (Calbiochem) and 0.6 mM of L-BAPA (Boehringer Mannheim). Human fibrinogen (Kabi-Vitrum) and β-amyloid peptides were added at 0.1 mg/ml. The assay volume was 0.9 ml. The reaction was monitored at 405 nm for 24–36 hours at intervals of 48 minutes at 25° C. Routinely, for the $k_{(app)}$ measurements: [t-PA]=$5 \times 10^{-10}$ M; [glu-plasminogen]=$5 \times 10^{-7}$ M; [fibrinogen]=$3.2 \times 10^{-7}$ M, when present; [BAPA]=0.6 mM. For the determination of the kinetic parameters, $k_{cat}$ and $K_m$: [t-PA]=$8 \times 10^{-11}$ M; [glu-plasminogen]=$1.7 \times 10^{-7}$ M to $7.3 \times 10^{-6}$ M; [fibrinogen]=$3.2 \times 10^{-7}$ M.

The concentration of plasmin was determined by active-site titration with p-nitrophenyl-p'-guanidinobenzoate (NPGB) (Chase, T. et al., Biochem. 8:2212–2224 (1969)). The concentration of active t-PA (one or two chains) was determined by NPGB titration with a tritant concentration four times higher than the one used for plasmin, due to the lower affinity of t-PA for the substrate. The determination of active t-PA by NPGB titration was confirmed in a standard assay with the substrate S-2288 (H-D-isoleucyl-L-propyl-L-arginine-p-nitroanilide; purchased from Kabi-Vitrum), according to the data supplied by ChromogenixAB, Sweden. The glu-plasminogen preparation was homogenous by sodium dodecyl sulfate-polyacrylamide electrophoresis. The yield of plasmin activity resulting from the conversion of the same lot of plasminogen was determined by measuring the plasmin activity after complete conversion by urokinase. Plasmin activity was correlated to plasmin concentration using a standard assay with S-2288 (H-D-isoleucyl-L-propyl-L-arginine-p-nitroanilide; ChromogenixAB, Sweden). Two-chain t-PA and plasmin-degraded fibrinogen were obtained by incubation with plasmin immobilized onto cross-linked Affigel-10. The gel was removed by centrifugation.

Figure 2:
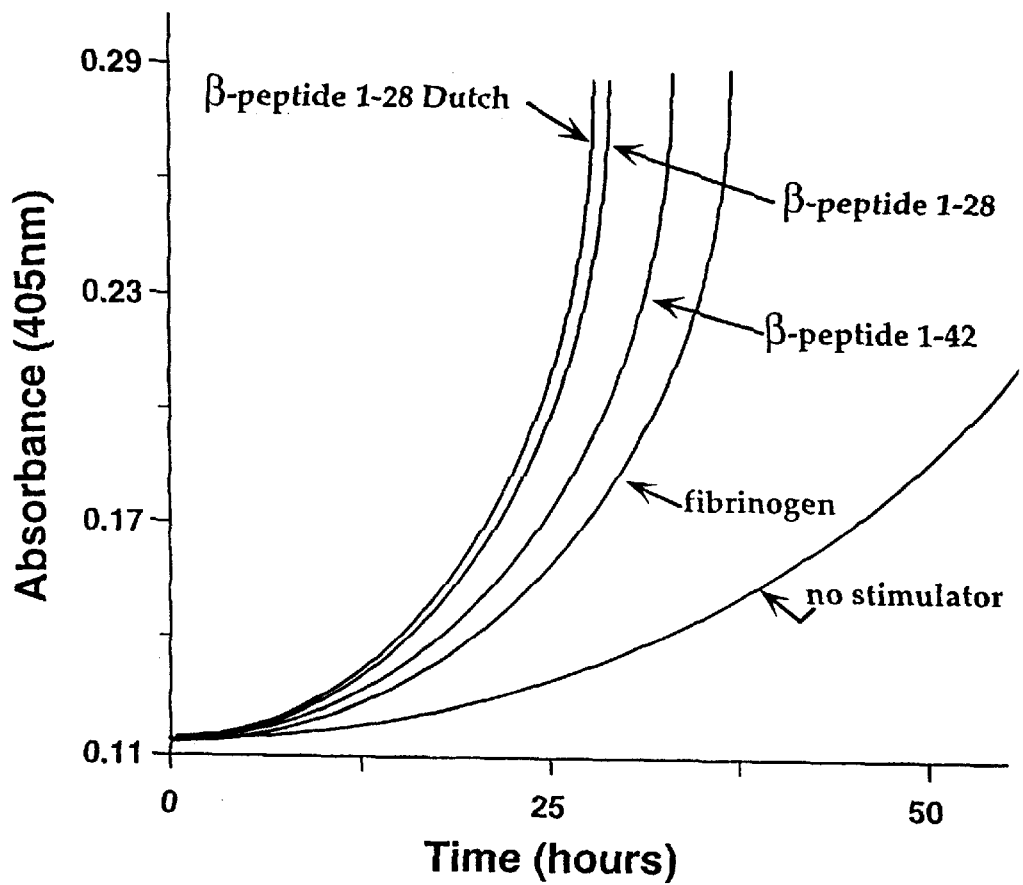
FIG. 2 provides kinetic data, under non-steady state conditions, for the activation of plasminogen by t-PA in the presence of various stimulators.

Absorbance was determined using a Kontron spectrophotometer, equipped with an automatic cell changer. The cuvette holder was connected to a thermostat-controlled water bath. The apparent first-order rate constant of activation k(app). was obtained by fitting the data to the equation:

$$Abs = a_{(BAPA)} [plg]_0 (t + 1/k_{(app)} e^{-k_{(app)} t} - 1/k_{(app)}) + Abs_0$$

where Abs is the absorbance at 405 rum. $[plg]_0$ is the initial concentration of plasminogen, $a_{(BAPA)}$ is the specific activity of plasmin towards BAPA, t is time, and $Abs_0$ is the initial absorbance. $k_{(app)}$ and $a_{(BAPA)}$ are independent variables. A non-linear regression program (Enzfitter, R. J. Leatherbarrow, Elsevier Scientific, NY, 1987) was used. The program was run with the initial plasminogen concentration as a constant and $a_{(BAPA)}$ and $Abs_0$ as variable parameters. The standard error obtained in the estimation of each of the variables was not greater than 10%. The curves presented in FIG. 2 are the curves corresponding to an average $k_{(app)}$ obtained with a minimum of two independent experiments; $a_{(BAPA)}$ and $Abs_0$ were normalized.

When the synthetic β-amyloid peptides were analyzed in this system in the unaggregated form, they were found to have a greater stimulatory effect upon t-PA than fibrinogen at the concentrations of peptide used (FIG. 2). There were only minor differences among the three peptides in the degree of stimulation. In a subsequent series of experiments the stimulatory effects of the β-amyloid peptides (unaggregated and aggregated forms), fibrinogen, and cyanogen bromide-generated fibrinogen fragments that have a stimulatory affect comparable to fibrin (Nieuwenhuizen, W. et al., Eur. J. Biochem. 174:163–169 (1988)) were examined. A number of control proteins were also tested and these included bovine serum albumin (BSA), ovalbumin, pyruvate kinase, and apoferritin. Corticotropin releasing factor (CRF) and growth hormone releasing factor (GRF) were also used as control peptides based upon the fact that they had similar sizes (41 and 29 amino acids respectively), a similar content of hydrophobic residues, and that the pI was either similar (CRF, pI 4.98) or opposite (GRF, pI 10.38) to the pI of the β-amyloid peptides. These peptides precipitated out of solution when the pH was adjusted to the theoretical pI and did not form fibrils.

Apparent first-order rate constants of plasminogen activation were obtained under non-steady state conditions (using 0.5 nM t-PA) by t-PA in the presence of different stimulators. The calculated apparent first-order rate constants of plasminogen activation in the presence and absence of these proteins (Table 1) showed that the β-amyloid peptides, unlike all of the control proteins, had a marked stimulatory effect upon the activity of t-PA. In Table 1, $k_{(app)}$ is the average±standard error of 2–6 independent experiments; protein was 0.1 mg/ml in each assay. Aggregated material was evaluated using either material stored for a short term ("S," designating the use of material that had been stored at 4° C. with 0.02% sodium azide for less than 2 weeks prior to assay), or material that had been stored for a long term ("L," designating the use of material that had been stored at 4° C. with 0.02% sodium azide for 6–10 weeks prior to assay).

TABLE 1

| Protein | k(app) |
| --- | --- |
| None | 1.7 ± 0.8 |
| Bovine Serum Albumin | 2.3 ± 0.8 |
| Ovalbumin | 1.3 ± 0.3 |
| Pyruvate Kinase | 2.0 ± 0.5 |
| Apoferritin | 2.0 ± 0.9 |
| Corticotropin Releasing Factor | 1.5 ± 0.6 |
| Growth Hormone Releasing Factor | 1.5 ± 0.4 |
| Fibrinogen | 7.8 ± 0.7 |
| CNBr-Fibrinogen Fragments | 65.4 ± 13.4 |
| β-Amyloid Peptides 1-28 Unaggregated | 13.9 ± 0.1 |
| β-Amyloid Peptides 1-28 Aggregated (S) | 12.1 ± 0.4 |
| β-Amyloid Peptides 1-28 Aggregated (L) | 67.7 ± 31.6 |
| β-Amyloid Peptides 1-28 Dutch, Unaggregated | 14.5 ± 0.1 |
| β-Amyloid Peptides 1-28 Dutch, Aggregated (S) | 17.0 ± 0.5 |
| β-Amyloid Peptides 1-28 Dutch, Aggregated (L) | 22.1 ± 9.1 |
| β-Amyloid Peptides 1-42 Unaggregated | 10.3 ± 0.2 |
| β-Amyloid Peptides 1-42 Aggregated (S) | 13.4 ± 0.4 |

There was little significant increase in the stimulatory effect with short term aggregation. However, after prolonged storage at 4° C. in the presence of 0.02% sodium azide, greater variation was observed in the effects of unaggregated versus aggregated forms of the peptides. With some aggregated samples first-order rate constants of activation at least fifty times higher than for unstimulated t-PA were obtained. These rates of activation are comparable to that obtained for fibrin. Thus, the highly aggregated forms of the peptides may have a more pronounced stimulatory affect on t-PA activity than unaggregated forms. The effects of the β-amyloid peptides 1–28 were evaluated in both aggregated and unaggregated forms on the activity of urokinase, the other major activator of plasminogen in the extrinsic fibrinolytic pathway. No stimulatory effect was detected.

In separate experiments, initial velocities of plasminogen activation by t-PA were obtained under steady state conditions, using a different assay system. The catalytic efficiencies are compared with those obtained through the determination of the apparent first-order rate constant of activation:

$$k_{(app)} \cong k_{cat}[t\text{-}PA]/K_m$$

and defined as $k_{cat}/K_m$ (app). The assays were carried out in the same assay medium as used above in the rate analysis. Initial velocities of plasminogen conversion to plasmin were calculated using the plasmin chromogenic substrate S-2251 (H-D-valyl-L-lysine-p-nitroanilide; Kabi-Vitrum).

Figure 3:
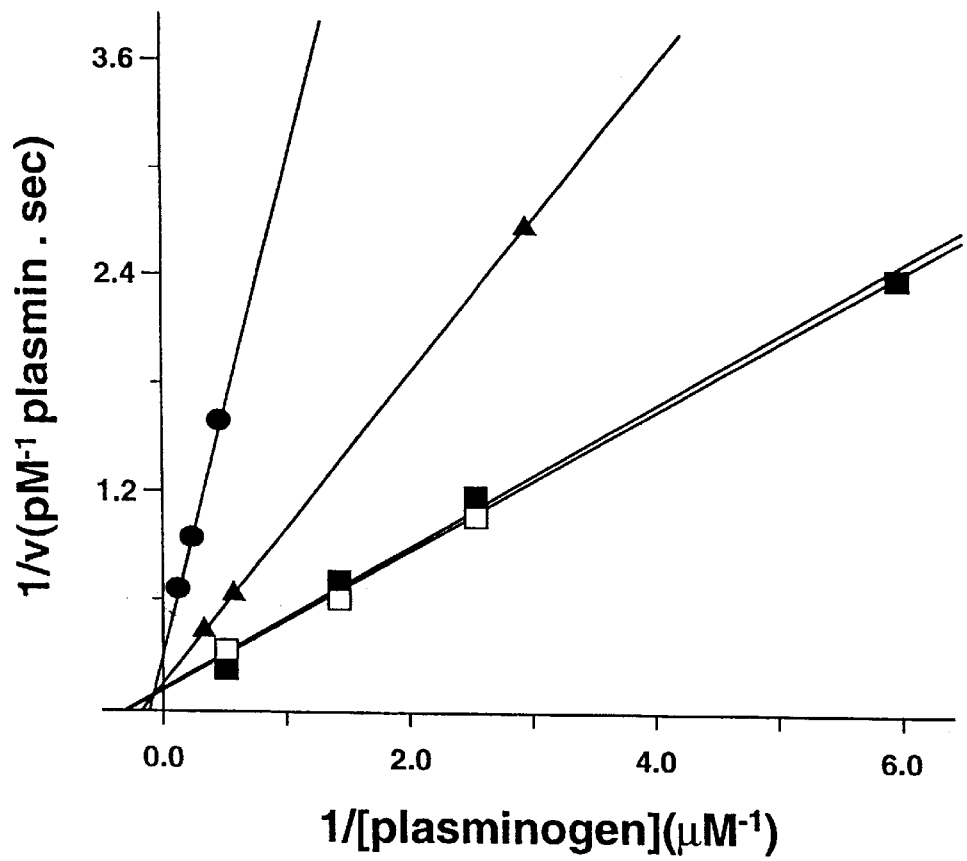
FIG. 3 is a Linfeweaver-Burk calculation of plasminogen activation by t-PA in the presence of fibrinogen (solid triangle), β-amyloid peptide 1–28 (solid square), and β-amyloid peptide 1–28 Dutch (open square), or in the absence of any protein stimulant (closed circles).

Lineweaver-Burk plots of plasminogen activation by t-PA in the absence or in the presence of fibrinogen or the unaggregated β-amyloid peptides 1–28 (FIG. 3) allowed the determination of $k_{cat}$ and $K_m$. With the β-amyloid peptides the $K_m$ was lower than for unstimulated t-PA and the $k_{cat}$ was higher, as observed for fibrinogen, but the changes were more pronounced. The catalytic efficiencies ($k_{cat}/K_m$) obtained in these assays confirmed the values of catalytic efficiency derived from the apparent first-order rate constant of plasminogen activation, obtained previously under non-steady state conditions (Table 1 and FIG. 3). The results of the kinetic data are summarized in Table 2.

TABLE 2

| Stimulator | $k_{cat}(s^{-1})$ | $K_m$ ($\mu M$) | $k_{cat}/K_m$ ($\mu M^{-1}s^{-1}$) | $k_{cat}/K_{m(app)}$ ($\mu M^{-1}s^{-1}$) |
| --- | --- | --- | --- | --- |
| None | 0.030 | 6.7 | 0.0045 | 0.0033 |
| Fibrinogen | 0.051 | 3.3 | 0.0155 | 0.0157 |
| β-Amyloid Peptide 1-28 | 0.058 | 1.9 | 0.305 | 0.0278 |
| β-Amyloid Peptide 1-28 Dutch | 0.058 | 1.8 | 0.0325 | 0.0290 |

In sum, the above Example shows that β-amyloid peptides are able to stimulate the activity of t-PA in vitro. In most cases of Alzheimer's Disease, β-amyloid peptides accumulate mainly as a cerebral parenchymal deposit rather than in vessel walls. This situation is in contrast to that seen in HCHWA-D in which blood vessels are predominantly affected. Experiments have suggested that the β-amyloid peptides in cerebral blood vessels originate in the vascular system (Tagliavini, F. et al., Lab. Investigation 62:761–767 (1990); Selkoe, D. J., Neurobiol. Aging 10:387–395 (1989); Haass; C. et al., Nature 359:322–325 (1992); Joachim, C. L. et al., Nature 341:226–230 (1989)). The different pattern of accumulation seen between the Alzheimer's amyloid peptide and the HCHWA-D β-amyloid peptide may be attributed to differences in hydrophilicity and/or isoelectric point. The mutation in the HCHWA-D peptide decreases the solubility and shifts the pI of the peptide closer to the pH of blood. These changes may thus result in β-amyloid peptides having different propensities to form fibrillar aggregates and thus contribute to the pronounced deposition of fibrils in the cerebrovascular system of HCHWA-D patients.

It has been suggested that the accumulation of β-amyloid within a blood vessel structurally weakens the vessel wall and eventually gives rise to hemorrhage (Torack, R. M., Amer. J. Pathol. 81:349–366 (1982)). The findings of the present invention indicate that the pathogenesis of brain disorders associated with the presence of β-amyloid fibrils is in part a consequence of inappropriate stimulation of plasminogen activation by t-PA. It is known that in blood, free plasmin is rapidly neutralized by alpha$_2$-antiplasmin. Thus, similar to what happens on a fibrin surface, t-PA and plasminogen can bind to the β-amyloid peptide fibrils and the newly formed bound plasmin can be protected from the action of alpha2-antiplasmin (Lijnen, H. R. et al., Semin. Thromb. Hemost. 8:2–10 (1982); Trang-Thang, C. et al., Blood 63:1331–1337 (1984)). Such a situation, if chronic, would provide a mechanism for damage to the blood vessel wall caused by β-amyloid peptide deposition. A high local concentration of plasmin could contribute to vessel damage leading to rupture of the vessel wall. This situation would be particularly relevant in HCHWA-D, where the accumulation of β-amyloid peptides within the vessel wall is extensive.

In sum, an analysis of the effects of β-amyloid peptides on t-PA has revealed that the β-amyloid peptides that characterize Alzheimer's Disease and HCHWA-D have a marked stimulatory affect upon plasminogen activation by t-PA, comparable to that of known stimulators of t-PA. This finding is significant in that it provides a means of investigating and controlling the pathogenesis of Alzheimer's Disease, HCHWA-D and CAA-related cerebral hemorrhage. It also provides an explanation for the deaths resulting from intracerebral hemorrhage that have occurred in patients undergoing t-PA or streptokinase treatment for acute cardiovascular disease (Pendlebury, W. W. et al., Annls. Neurol. 28:210–213 (1989); Wijdicks, E. P. M. et al., Stroke 24:554–557 (1993); Kase, C. S. et al., *Annls. Intern. Med.* 112:17–21 (1990)).

EXAMPLE 2

Active Site $^{125}$I Labeled Tissue-Type Plasminogen Activator Binds to Synthetic Amyloid Fibrils in a Kringle Dependent Manner Qualitative binding studies with radiolabeled tPA and amyloid fibrils were conducted. Using tPA:fibrin binding as a control, it was found that tPA binds to amyloid fibrils formed from β 1–28 and β 1–40 peptides. The addition of ε-aminocaproic acid to the binding mixtures was capable of competing out amyloid binding, thus indicating that tPA:amyloid binding was kringle dependent.

Active Site Radioiodination of the tPA-Peptidyl chloromethyl ketones irreversibly inhibit serine proteases by covalently binding the active site histidine. In this study, D-Tyr-Pro-Arg-chloromethyl ketone (Bachem Bioscience) was radioiodinated by the chloramine-T method and subsequently used to irreversibly bind to the active site of tPA. (Keyt, et al, *Anal. Biochem.* 206:73–83 (1992)). 1 mCi of I$^{125}$ was mixed with YPRck in 1 M Tris-HCL, 0.01% Tween 20 at pH 7.5. To initiate iodination 10 μl of 1 mg/ml Chloramine-T was added. After 1 minute, 20 μl of 1 mg/ml sodium metabisulfite was added to reduce the Chloramine-T and iodide. 15 μl of 1 mg/ml tPA was then added, and the mixture was incubated at room temperature for 1 hour to allow the YPRck to bind to the tPA. Radiolabeled tPA was purified from free iodine and unreacted YPRck using a PD10 column preequilibrated with PBS and 0.003% Tween 20. The labeled protein was stored at −20° C.

Synthetic Amyloid Fibril Formation—β1–28 (Chiron Mimotopes Peptide Systems) and β1–40 (Bachem Bioscience) peptides were dissolved in water. Aggregation solution conditions were 1×PBS, 1 mg/ml β-peptide and the pH was adjusted to the theoretical pI of the peptides (5.6 for β1–28 and 4.9 for β1–40). Solutions were kept at room temperature. Fibril formation was confirmed by light scattering and transmission electron microscopy.

Binding of Active Site-labeled tPA to Amyloid Fibrils or to Fibrin -tPA binding was determined by a modification of the method of Higgins and Vehar, *Biochem.* 26:7786–7791 (1987)). Labeled tPA at approximately 0.5 nM was combined with 0.1 mg/ml (final β-peptide fibrils in 1×PBS pH 7.4, 0.01% Tween 80 and 0.5% BSA. After 1 hour at 25° C., the mixtures were centrifuged at greater than 10,000 rpm to pellet the fibrils, Aliquots of the supernatant were counted for gamma emissions; Percentage labeled tPA bound to fibrils was determined by comparing the counts of the binding mixture to a control with no fibrils.

To confirm that the labeled tPA's protein binding surface was not altered by the radioiodination, it was bound to fibrin by substituting fibrinogen for the fibrils. Fibrin clot formation was initiated by adding 0.4 units/ml (final human thrombin. The remainder of the assay proceeded as above.

Inhibition of kringle-dependent labeled tPA Binding to Amyloid Fibrils and Fibrin Using ε-aminocaproic acid to the binding solutions were set up on the same manner as previously noted except that ε-aminocaproic acid at 0.1 M was included in the conditions.

The results of these experiments are presented in Table 3.

TABLE 3

| Sample | % tPA Bound |
| --- | --- |
| β 1-28 Amyloid Fibrils | 36% |
| β 1-40 Amyloid Fibrils | 62% |
| Fibrin | 58% |
| 1-28 Amyloid Fibrils with 0.1 M ε-aminocaproic acid | 7% |
| Fibrin with 0.1 M ε-aminocaproic acid | 13% |

EXAMPLE 3 t-PA and its Antagonists in the Treatment of Alzheimer's Disease and Other Neurological Disorders It has been shown that some epitopes on fibrinogen cross-react immunologically with amyloid β peptide epitopes and vice versa (Stern, R. A. et al., *FEBS Lett.* 264:43–47 (1990)). This observation is extended by showing that the Alzheimer's amyloid β peptide is a strong stimulator of the t-PA-mediated plasminogen activation reaction (Kingston, I. B. et al., *Nature Medicine* 1:138–142 (1995)). One aspect of the present invention reflects the interpretation of this observation as indicating that such cross-reactivity extends to function as well as structure.

Aged solutions of fibrillar β peptide have been found to have stimulatory activities comparable to the most potent known natural stimulators of this reaction, fibrinogen and fibrin. To further investigate this relationship, the ability of amyloid β peptide fibrils to stimulate tissue plasminogen activator was studied. For this purpose, plasminogen activation assays were carried out as described by Bennett, W. F. et al., *J. Biol. Chem.* 266:5191–5201 (1991)). Plasmin generation was monitored by measuring the absorbance change at 405 nm produced by hydrolysis of the substrate, H-D-valyl-L-leucyl-L-lysine-p-nitroanilide. Stimulators tested were present in the assay at a concentration of 56 μg/ml. The apparent first-order rate constants of plasminogen activation by t-PA were measured for various stimulators. Rate constants were determined as described by Castro, M. J. M.; et al., *Analyt. Biochem.* 226:225–231 (1995)) using fresh or aged amyloid β peptide fibrils or control proteins.

A Michaelis-Menten analysis of this reaction indicated that, as with these physiological stimulators, both $k_{cat}$ and $K_m$ of t-PA were affected by the presence of the amyloid β peptide. This rate-enhancement phenomenon has been shown, in the case of fibrin(ogen), to be an allosteric effect due to binding of the stimulator to t-PA and a consequent conformational change involving a rearrangement of the active site residues of the protease domain (Higgins, D. L. et al., *Fibrinolysis* 6:161–166 (1992); Madison, E. L. et al., *Science* 262:419–421 (1993)).

The present invention derives, in part, from the appreciation that the interaction of t-PA and plasminogen with the Alzheimer's amyloid β peptide involves ion pairs between positive and negative charges on the surface of the β peptide (and/or its fibrils) and the bipolar ligand binding pocket of the kringles. This supposition was, in part, supported by the fact that subfragment analysis of fibrin had identified a stretch of amino acids between residues 148–160 of the fibrin Aa chain as the crucial region for t-PA stimulation (Schielen, W. J. G. et al., *Fibrinolysis* 7:63–67 (1993)). This portion of the polypeptide chain has an extremely high β strand propensity with positively and negatively charged residues alternating with neutral residues. From fiber diffraction studies, a cross β structure with a bipolar charged surface has also been proposed for the structure of the β-amyloid fibril (Kirschner, D. A. et al., *Proc. Natl. Acad. Sci. USA* 84:6953–6957 (1987)).

Previous studies of the interaction of human tissue plasminogen activator with the amyloid β peptide employed a functional plasminogen activation assay (Kingston, I. B. et al., *Nature Medicine* 1:138–142 (1995); Castro, M. J. M., et al., *Analyt. Biochem.* 226:225–231 (1995)). However, to understand this interaction more fully, a sensitive and quantitative assay for measuring direct amyloid β peptide binding by t-PA and other fibrin(ogen)-binding proteins (e. g., plasmin) was employed in the present invention. For this purposed a specific probe molecule, D-Tyr-Pro-Arg chloromethyl ketone (YPACK), was radioiodinated with $^{125}$I then reacted with t-PA, plasmin, and thrombin to effect covalent active site modification of their respective protease domains (Keyt, B. A. et al., *Analyt. Biochem.* 206:73–83 (1992)). Binding of $^{125}$I-YPACK-modified t-PA to fibrin and amyloid β peptide fibrils was carried out by a modification of the method of Higgins, D. L. et al. (*Fibrinolysis* 6:161–166 (1992)). Incubations of t-PA (0.5 nM) with fibrin or fibrils (100 μg/ml) were in 1× phosphate buffered saline, 0.01% Tween-80, 0.5% bovine serum albumin, pH 7.4, for 60 min. at 37° C. In some instances, ε-amino caproic acid (ε-ACA) was also present at a concentration of 100 mM. This accomplished three things: (i) it attached a single, high specific activity label to the proteins; (ii) it modified each protein molecule at a unique position (a covalent adduct to the serine and histidine of the catalytic triad); and (iii) it irreversibly inhibited the protease activity, thus preventing complications due to proteolysis of the peptides.

Using this material t-PA could be shown to bind to β1–28 and β1–40 fibrils with a $K_d$ in the sub-nanomolar range, comparable to its affinity for fibrin. In addition, the experiment showed that the specific antagonist, ε-amino caproic acid (ε-ACA), which is known to interfere with kringle domain-mediated fibrin binding by t-PA, also partially blocked t-PA's interaction with the amyloid β fibrils. This finding is consistent with the conclusion of the present invention that t-PA interacts with the amyloid β fibrils, and that such interactions may involve electrostatic interactions mediated by the bipolar ligand binding pocket of the t-PA kringle two domain (see Table 3).

Since the primary ligand binding site on a kringle domain is a bipolar pocket, it was hypothesized that the kringle-amyloid β peptide interaction was effected by oppositely charged amino acid side chains projecting from the surface of the β-amyloid fibril with a spacing of approximately 6–9 Å (the length of the pocket). In a cross β structure such as is found in the amyloid fibril (Kirschner, D. A. et al., *Proc. Natl. Acad. Sci. USA* 84:6953–6957 (1987)) the charged side chains may project from either i+2 or i–2 amino acids in the same strand (6.4–7.2 Å apart) or from i+2 or i–2 amino adds in adjacent strands (8.0–8.7 Å apart); in either case, assuming a modest amount of flexibility in the side chain, the spacing of the opposite charges on the fibril surface would conform to the dimensions of the bipolar kringle ligand binding pocket. There are twelve charged residues both in the full length amyloid β peptide and in the shortened β(1–28) version: six negatively charged (Asp1, Glu3, Asp7, Glu11, Glu22, and Asp23) and six positively charged (Arg5, His6, His13, His14, Lys16, and Lys28).

To develop a higher resolution map of the molecular determinants of the t-PA-fibril and plasmin-fibril interaction, charged amino acids were "mutated" one at a time with glutamine substitutions. Twelve variants of the Parent β(1–28) peptide were synthesized, each with a different one of the twelve charged amino adds changed to a glutamine residue (except for the N-terminal Asp, which was mutated to Asn instead of Gln to prevent spontaneous pyroglutamic add formation). The "Charged→Gln" β(1–28) peptide analogs for mapping the determinants of t-PA/plasmin binding and plasminogen activation are shown in Table 4. In each peptide sequence the mutated residue is shown in boldface.

Table 4

| NAME | SEQ ID NO | SEQUENCE |
| --- | --- | --- |
| Parent | 2 | DAEFRHDSGYEVHHQKLVFFAEDVGSNK |
| D1N | 3 | NAEFRHDSGYEVHHQKLVFFAEDVGSNK |
| E3Q | 4 | DAQFRHDSGYEVHHQKLVFFAEDVGSNK |
| R5Q | 5 | DAEFQHDSGYEVHHQKLVFFAEDVGSNK |
| H6Q | 6 | DAEFRQDSGYEVHHQKLVFFAEDVGSNK |
| D7Q | 7 | DAEFRHQSGYEVHHQKLVFFAEDVGSNK |
| E11Q | 8 | DAEFRHDSGYQVHHQKLVFFAEDVGSNK |
| H13Q | 9 | DAEFRHDSGYEVQHQKLVFFAEDVGSNK |
| H14Q | 10 | DAEFRHDSGYEVHQQKLVFFAEDVGSNK |
| K16Q | 11 | DAEFRHDSGYEVHHQQLVFFAEDVGSNK |
| E22Q | 12 | DAEFRHDSGYEVHHQKLVFFAQDVGSNK |
| D23Q | 13 | DAEFRHDSGYEVHHQKLVFFAEQVGSNK |
| K28Q | 14 | DAEFRHDSGYEVHHQKLVFFAEDVGSNQ |

Glutamine was chosen as the preferred amino acid for these substitutions for several reasons. Perutz and coworkers have shown that glutamine-rich peptides spontaneously form β-sheet structures in solution, indicating that this is an energetically favorable secondary structure environment for glutamine (Perutz, M. F. et al.,. *Proc. Natl. Acad. Sci. (U.S.A.)* 91:5355–5358 (1994)). Glutamine also has a long, hydrophilic side chain that is frequently found on the surfaces of proteins, and it can hydrogen bond both with acidic residues (Asp and Glu) and with basic residues (Lys, Arg, His), so it should be able to maintain a near-normal hydrogen bonding pattern on the surface of the amyloid fibril and thus minimally disrupt its structure. Finally, even though glutamine is a hydrophilic substitution it is uncharged, and eliminating the charge should be sufficient to significantly lower the fibril's affinity to fibrin binding proteins. An analogous mutation, Asp238→Asn, in the bipolar ligand binding pocket of t-PA kringle two has been shown to abolish fibrin binding (Anderson, S. et al., U.S. Pat. No. 5,366,886).

The twelve β1–28 peptide analogs were used for plasminogen activation and direct binding assays with the fibrinogen-binding proteins t-PA, plasmin, and thrombin,, specifically labeled at their respective protease domain active sites as described above. For five of the peptide variants R5Q, H6Q, K16Q, D23Q, and K28Q, t-PA binding was reduced relative to its binding to both wt β1–28 and fibrin controls, implying that the t-PA binding "footprint" on the fibrils was rather large. Tissue plasminogen activator interactions with fibrin are mediated by at least three of its five domains: kringle two, the fibronectin-like finger domain, and the protease. Thus, the t-PA-fibrin molecular interface must be extensive, and the above results with the mutant amyloid β fibrils suggest likewise that the t-PA-fibril complex involves intermolecular contacts at multiple points on the surfaces of both the fibril and the t-PA molecule.

By contrast, the plasmin-fibril interaction appeared to involve primarily the charges on Lys16 and Lys28 of the amyloid β peptide; this is consistent with the fact that plasmin has no fibronectin-like finger domain and is thought to interact with fibrin primarily through the lysine binding pockets on kringles 1 and 4. Both Lys16 and Lys28 are also among those residues that mediate the t-PA-fibril interaction. Interestingly, in the functional plasminogen activation stimulation assay, the β1–28 K28Q variant exhibited profoundly decreased levels of stimulation, indicating that this may be the key residue involved in the amyloid β peptide-induced conformational change at the t-PA active site that leads to increased efficiency of the plasminogen cleavage reaction. Also interesting was the fact that the β1–28 K16Q variant exhibited enhanced stimulation, perhaps indicating that binding of t-PA and/or plasminogen at Lys16 in the wild type peptide results in a relatively inactive conformation meaning, in effect, that the lysine side chain at residue 16 is a competitive inhibitor of the stimulation reaction and thus mutation of this lysine leads to increased stimulation. Little if any binding of radioiodinated thrombin to the amyloid β peptide fibrils was observed. The fibrinogen-binding exosite is near to the active site in the thrombin protease domain, and it is possible that the chemical modification of this active site with a bulky iodinated tripeptide resulted in steric hindrance of binding.

It had been possible that some of the charged→glutamine peptide variants might not form fibrils. However, one aspect of the present invention concerns the determination, by electron microscopy, that all of the peptides form bona fide fibrils having normal-appearing morphology. It was further determined that t-PA stimulation activity is correlated with fibril formation, i. e., that soluble, non-fibrillar amyloid β peptides do not stimulate t-PA. This is particularly noteworthy in light of the known correlation of peptide neurotoxicity with fibril formation (Simmons, L. K. et al., *Molecular Pharmacology* 45, 373–379 (1994)) and the recent findings that t-PA can mediate excitotoxicity in the hippocampus (see, Tsirka, S. E. et al., *Nature* 377:340–344 (1995)).

The findings of the present invention have significant implications for Alzheimer's Disease. The plasminogen activators urokinase and t-PA are known to be involved in neurite outgrowth, perhaps as promoters of tissue remodeling or adhesion/deadhesion cycles (Pittman, R. N. et al., *J. Neurosci.* 9, 4269–4286 (1989)). However, it is not known if these enzymes exert their effects via plasminogen, a plasminogen-like protein, or a cell surface receptor. Although both urokinase and t-PA use plasminogen as a substrate, urokinase does not bind to fibrin nor is it stimulated by the amyloid β peptide (Kingston, I. B. et al., *Nature Medicine* 1:138–142 (1995)).

Tissue plasminogen activator is expressed in hippocampal neurons of the adult mouse CNS and has been correlated with synaptic plasticity (Sappino, A. P. et al., *J. Clin. Invest.* 92:679–685 (1993)). In a rat memory model, t-PA mRNA was shown to be induced by neuronal activity during long-term potentiation, seizure and kindling (Qian, Z. et al., *Nature* 361:453–457 (1993)). A role for t-PA in neurodegeneration has also been demonstrated using t-PA$^{-/-}$ knock-out mice; such animals are resistant to neuronal cell loss in the hippocampus induced by glutamate receptor agonists, indicating that t-PA plays a role in the phenomenon of excitotoxicity (Tsirka, S. E. et al., *Nature* 377:340–344 (1995)).

Both t-PA and thrombin have been found associated with senile plaques from the brains of Alzheimer's patients (Rebeck, G. W. et al., *Neurobiol. Aging* 15, Suppl. 1, a483 (1994); Akiyama, H. et al., *Neurosci. Lett.* 146:152–154 (1992); Akiyama, H. et al., *Neurobiol. Aging* 15, Suppl. 1:a511 (1994)). It is likely that fibrin-binding proteins in the cerebral spinal fluid are effectively concentrated in the region of amyloid and pre-amyloid deposits by virtue of their intrinsic affinity for the amyloid β peptide.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of identifying mutant t-PA derivatives as improved thrombolytic therapies with decreased potential for vascular hemorrhage comprising:

(a) mutating one or more amino acids of t-PA;
   (b) measuring binding of the mutant t-PA with β-amyloid peptide; and
   (c) measuring binding of the mutant t-PA with fibrin: wherein a t-PA mutant which binds to fibrin but does not bind to β-amyloid peptid is identified as an improved thrombolytic therapy.

* * * * *

UNITED STATES PATENT AND TRADEMARK OFFICE
CERTIFICATE OF CORRECTION

PATENT NO. : 6,136,548
DATED : Oct. 24, 2000
INVENTOR(S) : Stephen Anderson

It is certified that error appears in the above-identified patent and that said Letters Patent are hereby corrected as shown below:

At Col. 19, Line 39, please delete "[t-PA]=5x10 $^{31}$ $^{10}$M" and insert therefor --[t-PA]=5x10$^{-10}$M--

At Col. 20, Line 11, please delete "405 rum" and insert therefor --405 nm--

At Col. 22, Line 67, please delete "E. P. M." and insert therefor --E. F. M.--

At Col. 23, Line 62, please delete "thrombin" and insert therefor --thrombin)--

At Col. 26, Line 6, please delete "add formation" and insert therefor --acid formation--

Signed and Sealed this

Eighth Day of May, 2001

Attest:

NICHOLAS P. GODICI

Attesting Officer     Acting Director of the United States Patent and Trademark Office

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 42 amino acids
      (B) TYPE: amino acid
      (D) TOPOLOGY: linear (ii) MOLECULE TYPE: peptide (iii) HYPOTHETICAL: NO (v) FRAGMENT TYPE: N-terminal (vi) ORIGINAL SOURCE:
      (A) ORGANISM: AMYLOID PEPTIDE (xi) SEQUENCE DESCRIPTION: SEQ ID NO:1:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

(2) INFORMATION FOR SEQ ID NO:2:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: HOMO SAPIENS (vii) IMMEDIATE SOURCE:
        (B) CLONE: B(1-28) peptide of amyloid B protein (xi) SEQUENCE DESCRIPTION: SEQ ID NO:2:

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

(2) INFORMATION FOR SEQ ID NO:3:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
        (A) ORGANISM: HOMO SAPIENS (vii) IMMEDIATE SOURCE:
        (B) CLONE: D1N B(1-28) peptide of amyloid B protein (xi) SEQUENCE DESCRIPTION: SEQ ID NO:3:

Asn Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

(2) INFORMATION FOR SEQ ID NO:4:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
             (A) ORGANISM: HOMO SAPIENS (vii) IMMEDIATE SOURCE:
              (B) CLONE: E3Q B(1-28) peptide of amyloid B protein (xi) SEQUENCE DESCRIPTION: SEQ ID NO:4:

Asp Ala Gln Phe Arg His Asp Ser Gly Tyr Glu Val His His Gln Lys
1               5                  10                  15

Leu Val Phe Phe Ala Glu Asp Val Gly Ser Asn Lys
            20                  25

(2) INFORMATION FOR SEQ ID NO:5:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (iii) HYPOTHETICAL: YES (v) FRAGMENT TYPE: N-terminal (vi) ORIGINAL SOURCE:
             (A) ORGANISM: HOMO SAPIENS (vii) IMMEDIATE SOURCE:
              (B) CLONE: R5Q B(1-28) peptide of amyloid B protein (xi) SEQUENCE DESCRIPTION: SEQ ID NO:5:

Asp Ala Glu Phe Gln His Asp Ser Gly Tyr Glu Val His His Gln Lys
1               5                  10                  15

Leu Val Phe Phe Ala Glu Asp Val Gly Ser Asn Lys
            20                  25

(2) INFORMATION FOR SEQ ID NO:6:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (iii) HYPOTHETICAL: YES (v) FRAGMENT TYPE: N-terminal (vi) ORIGINAL SOURCE:
             (A) ORGANISM: HOMO SAPIENS (vii) IMMEDIATE SOURCE:
              (B) CLONE: H6Q B(1-28) peptide of amyloid B protein (xi) SEQUENCE DESCRIPTION: SEQ ID NO:6:

Asp Ala Glu Phe Arg Gln Asp Ser Gly Tyr Glu Val His His Gln Lys
1               5                  10                  15

Leu Val Phe Phe Ala Glu Asp Val Gly Ser Asn Lys
            20                  25

(2) INFORMATION FOR SEQ ID NO:7:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (iii) HYPOTHETICAL: YES (v) FRAGMENT TYPE: N-terminal (vi) ORIGINAL SOURCE:
         (A) ORGANISM: HOMO SAPIENS (vii) IMMEDIATE SOURCE:
         (B) CLONE: D7Q B(1-28) peptide of amyloid B protein (xi) SEQUENCE DESCRIPTION: SEQ ID NO:7:

Asp Ala Glu Phe Arg His Gln Ser Gly Tyr Glu Val His His Gln Lys
1               5                  10                  15

Leu Val Phe Phe Ala Glu Asp Val Gly Ser Asn Lys
            20                  25

(2) INFORMATION FOR SEQ ID NO:8:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
         (A) ORGANISM: HOMO SAPIENS (vii) IMMEDIATE SOURCE:
         (B) CLONE: E11Q B(1-28) peptide of amyloid B protein (xi) SEQUENCE DESCRIPTION: SEQ ID NO:8:

Asp Ala Glu Phe Arg His Asp Ser Gly Tyr Gln Val His His Gln Lys
1               5                  10                  15

Leu Val Phe Phe Ala Glu Asp Val Gly Ser Asn Lys
            20                  25

(2) INFORMATION FOR SEQ ID NO:9:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
         (A) ORGANISM: HOMO SAPIENS (vii) IMMEDIATE SOURCE:
         (B) CLONE: H13Q B(1-28) peptide of amyloid B protein (xi) SEQUENCE DESCRIPTION: SEQ ID NO:9:

Asp Ala Glu Phe Arg His Asp Ser Gly Tyr Glu Val Gln His Gln Lys
1               5                  10                  15

Leu Val Phe Phe Ala Glu Asp Val Gly Ser Asn Lys
            20                  25

(2) INFORMATION FOR SEQ ID NO:10:

```
    (i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
        (A) ORGANISM: HOMO SAPIENS (vii) IMMEDIATE SOURCE:
        (B) CLONE: H14Q B(1-28) peptide of amyloid B protein (xi) SEQUENCE DESCRIPTION: SEQ ID NO:10:

Asp Ala Glu Phe Arg His Asp Ser Gly Tyr Glu Val His Gln Gln Lys
1               5                  10                  15

Leu Val Phe Phe Ala Glu Asp Val Gly Ser Asn Lys
            20                  25

(2) INFORMATION FOR SEQ ID NO:11:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
        (A) ORGANISM: HOMO SAPIENS (vii) IMMEDIATE SOURCE:
        (B) CLONE: K16Q B(1-28) peptide of amyloid B protein (xi) SEQUENCE DESCRIPTION: SEQ ID NO:11:

Asp Ala Glu Phe Arg His Asp Ser Gly Tyr Glu Val His His Gln Gln
1               5                  10                  15

Leu Val Phe Phe Ala Glu Asp Val Gly Ser Asn Lys
            20                  25

(2) INFORMATION FOR SEQ ID NO:12:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
        (A) ORGANISM: HOMO SAPIENS (vii) IMMEDIATE SOURCE:
        (B) CLONE: E22Q B(1-28) peptide of amyloid B protein (xi) SEQUENCE DESCRIPTION: SEQ ID NO:12:

Asp Ala Glu Phe Arg His Asp Ser Gly Tyr Glu Val His His Gln Lys
1               5                  10                  15
```

```
Leu Val Phe Phe Ala Gln Asp Val Gly Ser Asn Lys
            20                  25

(2) INFORMATION FOR SEQ ID NO:13:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
        (A) ORGANISM: HOMO SAPIENS (vii) IMMEDIATE SOURCE:
        (B) CLONE: D23Q B(1-28) peptide of amyloid B protein (xi) SEQUENCE DESCRIPTION: SEQ ID NO:13:

Asp Ala Glu Phe Arg His Asp Ser Gly Tyr Glu Val His His Gln Lys
1               5                   10                  15

Leu Val Phe Phe Ala Glu Gln Val Gly Ser Asn Lys
            20                  25

(2) INFORMATION FOR SEQ ID NO:14:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: YES (v) FRAGMENT TYPE: N-terminal (vi) ORIGINAL SOURCE:
        (A) ORGANISM: HOMO SAPIENS (vii) IMMEDIATE SOURCE:
        (B) CLONE: K28Q B(1-28) peptide of amyloid B protein (xi) SEQUENCE DESCRIPTION: SEQ ID NO:14:

Asp Ala Glu Phe Arg His Asp Ser Gly Tyr Glu Val His His Gln Lys
1               5                   10                  15

Leu Val Phe Phe Ala Glu Asp Val Gly Ser Asn Gln
            20                  25
```